United States Patent
Cathomen et al.

(10) Patent No.: US 12,428,492 B2
(45) Date of Patent: Sep. 30, 2025

(54) CHIMERIC ANTIGEN RECEPTORS THAT BIND TO PROSTATE SPECIFIC MEMBRANE ANTIGEN

(71) Applicant: Albert-Ludwigs-Universitaet Freiburg, Freiburg (DE)

(72) Inventors: Toni Cathomen, Freiburg (DE); Philipp Wolf, Sexau (DE); Jamal Alzubi, Freiburg (DE); Susanne Schultze-Seemann, Merzhausen (DE); Irina Kuckuck, Freiburg (DE)

(73) Assignee: Albert-Ludwigs-Universitaet Freiburg, Freiburg (DE)

( * ) Notice: Subject to any disclaimer, the term of this patent is extended or adjusted under 35 U.S.C. 154(b) by 0 days.

(21) Appl. No.: 17/788,723

(22) PCT Filed: Dec. 14, 2020

(86) PCT No.: PCT/EP2020/086003
§ 371 (c)(1),
(2) Date: Jun. 23, 2022

(87) PCT Pub. No.: WO2021/130042
PCT Pub. Date: Jul. 1, 2021

(65) Prior Publication Data
US 2023/0039030 A1 Feb. 9, 2023

(30) Foreign Application Priority Data
Dec. 23, 2019 (EP) ..................... 19219238

(51) Int. Cl.
| C07K 16/30 | (2006.01) |
| A61K 39/00 | (2006.01) |
| A61K 40/11 | (2025.01) |
| A61K 40/31 | (2025.01) |
| A61K 40/42 | (2025.01) |
| A61P 35/00 | (2006.01) |

(52) U.S. Cl.
CPC .......... C07K 16/3069 (2013.01); A61K 40/11 (2025.01); A61K 40/31 (2025.01); A61K 40/4276 (2025.01); A61P 35/00 (2018.01); C07K 2317/565 (2013.01); C07K 2317/622 (2013.01); C07K 2319/02 (2013.01); C07K 2319/03 (2013.01)

(58) Field of Classification Search
None
See application file for complete search history.

(56) References Cited

U.S. PATENT DOCUMENTS 8,632,777 B2 * 1/2014 Elsasser-Beile ........ A61P 31/00
424/135.1
2022/0402998 A1 * 12/2022 Liu ..................... A61K 35/17

FOREIGN PATENT DOCUMENTS

| WO | WO 2006/125481 A1 | 11/2006 | |
| WO | WO 2010/037836 A2 | 4/2010 | |
| WO | WO 2018/111340 A1 | 6/2018 | |
| WO | WO-2018187791 A1 * | 10/2018 | .......... C07K 14/705 |
| WO | WO-2019232503 A1 * | 12/2019 | ............. A61K 35/17 |

OTHER PUBLICATIONS

Almagro & Fransson, Frontiers in Bioscience 2008; 13:1619-33 (Year: 2008).*
Hummel et al. (J. Clin. Oncology May 26, 2019) (Year: 2019).*
Hassani et al. (Iranian J. Biotech. Jul. 2017, pp. 183-184: Ab No. PS-141) (Year: 2017).*
Hombach et al. (Gene Therapy 2010 17: 1206-1213) (Year: 2010).*
Song et al. (Int. J. Surgery 2018: 133-140) (Year: 2018).*
M. Hassani et al., *J. of Cell. Biochem.*, vol. 120, No. 6, pp. 10787-10795 (Jan. 22, 2019).
J. Alzubi et al., *Human Gene Therapy*, vol. 29, No. 12, pp. A21 (Dec. 1, 2018).
U. Elsaesser-Beile et al., *Int. J. Mol. Med.*, vol. 26, supplement 1, pp. 550 (Jan. 1, 2010).
M. Cartellieri et al., *Blood*, vol. 126, No. 23, pp. 5549 (Nov. 30, 2015).
S.P. Santoro et al., *Cancer Immunol. Res.*, vol. 3, No. 1, pp. 68-84 (Jan. 1, 2015).
Q. Ma et al., *The Prostate*, vol. 74, No. 3, pp. 286-296 (Feb. 1, 2014).
X. S. Zhong et al., *Mol. Therapy*, vol. 18, No. 2, pp. 413-420 (Feb. 1, 2010).
Communication under Article 94(3) EPC issued by the European Patent Office on Jul. 28, 2023 in connection with European Patent Application No. 20 821 244.9.
Claims 1-13 addressed in the Communication under Article 94(3) EPC issued by the European Patent Office on Jul. 28, 2023 in connection with European Patent Application No. 20 821 244.9.
Applicant's Reply filed Nov. 22, 2023 in response the Communication under Article 94(3) EPC issued by the European Patent Office on Jul. 28, 2023 in connection with European Patent Application No. 20 821 244.9.

* cited by examiner

*Primary Examiner* — Peter J Reddig
(74) *Attorney, Agent, or Firm* — Smith Patent, LLC; Chalin A. Smith

(57) ABSTRACT

The present invention relates to a novel chimeric antigen receptor (CAR) comprising an antigen-binding fragment which binds specifically to PSMA antigen, and a method of manufacturing high-quality CAR T cell products by transfection and/or transduction of T cells therewith, which allows to effectively treat tumors in vivo alone or in combination with pharmaceutical drugs, such chemotherapies, biopharmaceutical drugs, such as antibodies, or small-molecule drugs, such as protein kinase inhibitors.

12 Claims, 24 Drawing Sheets

Specification includes a Sequence Listing.

nt and aa sequences of humanized VH chains of scFv A5 hum A5-VH1

*nt sequence (coding strand)* (SEQ ID NO:15)

GACGTGAAACTCGTGGAATCAGGCGGTGGGTTGGTTAAACCGGGTGAATCCCTCCG
CCTCTCTTGCGCGGCGAGCGGGTTCACATTTTCAGATTATTATATGTATTGGATCCGA
CAAACTCCTGAAAAACGGCTTGAATGGGTTGCCATTATTTCAGATGGCGGATATTACA
CTTACTATTCTGACATTGTGAAAGGTCGCTTTACAATCTCCAGGGACAATGCGAAAAA
CAACCTGTACTTGCAAATGTCTAGCCTGCGATCAGAGGATACTGCAATGTACTACTGC
ACCCGCGGATTTCCGCTTCTGCGACATGGAGCTATGGACTACTGGGGTCTCGGCAC
GAGTGTAACGGTGAGTAGT

*aa sequence* (grey: CDR regions, IMGT numbering) (SEQ ID NO:16)

DVKLVESGGGLVKPGESLRLSCAASGFTFSDYYMYWIRQTPEKRLEWVAIISDGGYYTYY
SDIVKGRFTISRDNAKNNLYLQMSSLRSEDTAMYYCTRGFPLLRHGAMDYWGLGTSVTV
SS hum A5-VH2

*nt sequence (coding strand)* (SEQ ID NO:17)

CAAGTCCAACTGGTGGAATCTGGTGGTGGTCTTGTTAAACCAGGGGAAAGTCTGCGA
CTGAGCTGCGCCGCGAGTGGGTTCACGTTTTCCGACTACTATATGAGCTGGATTAGA
CAGACGCCTGAGAAACGACTCGAGTGGGTTAGTATTATTAGTGATGGAGGGTATTAC
ACCTACTATGCAGATATCGTTAAAGGGCGATTTACTATCAGCCGAGATAACGCAAAAA
ACAACTTGTATCTCCAAATGTCCTCACTGCGGGCTGAGGATACCGCTGTATATTACTG
TACCAGGGGTTTTCCTCTCCTGCGGCACGGGGCTATGGATTATTGGGGTTTGGGGAC
CTCAGTTACGGTATCATCC

*aa sequence (grey: CDR regions, IMGT numbering)* (SEQ ID NO:18)

QVQLVESGGGLVKPGESLRLSCAASGFTFSDYYMSWIRQTPEKRLEWVSIISDGGYYTYY
ADIVKGRFTISRDNAKNNLYLQMSSLRAEDTAVYYCTRGFPLLRHGAMDYWGLGTSVTV
SS

Fig. 1 hum A5-VH3

*nt sequence (coding strand)* (SEQ ID NO:19)

CAGGTACAACTGGTGGAAAGCGGGGGAGGACTTGTCAAGCCCGGAGGGTCCCTCAG
ATTGAGCTGTGCGGCCTCCGGGTTCACCTTTTCCGATTACTATATGTCCTGGATTCGG
CAGGCACCGGGTAAGGGATTGGAGTGGGTATCTTATATAAGCGACGGGGGCTATTAT
ACTTATTACGCTGATAGTGTGAAAGGGCGCTTCACTATCAGCCGAGACAATGCGAAG
AATTCTTTGTATTTGCAGATGAATTCTTTGAGAGCCGAGGATACAGCGGTTTATTACTG
TACGAGAGGGTTTCCACTTCTGAGGCATGGTGCGATGGATTATTGGGGACTGGGTAC
TAGCGTCACCGTAAGCTCT

*aa sequence (grey: CDR regions, IMGT numbering)* (SEQ ID NO:20)

QVQLVESGGGLVKPGGSLRLSCAASGFTFSDYYMSWIRQAPGKGLEWVSYISDGGYYT
YYADSVKGRFTISRDNAKNSLYLQMNSLRAEDTAVYYCTRGFPLLRHGAMDYWGLGTSV
TVSS hum A5-VH4

*nt sequence (coding strand)* (SEQ ID NO:21)

CAAGTACAGTTGGTTGAAAGTGGTGGCGGCCTCGTTAAGCCTGGCGGATCTCTGAGA
TTGTCTTGTGCTGCGTCTGGATTCACTTTTTCCGACTATTATATGTATTGGGTGAGACA
GACACCAGAAAAAAGGCTTGAATGGGTCGCCATAATATCCGATGGGGGTTATTATACT
TACTACGCTGACAGCATAAAAGGGAGATTCACGATAAGCCGGGATAATGCCAAAAATA
GTCTTTATCTCCAAATGAACTCTCTGAGAGCGGAAGATACTGCTGTATACTATTGCAC
TAGAGGGTTCCCATTGTTGAGACATGGAGCAATGGATTACTGGGGCAAGGGACTCT
CGTAACCGTCTCATCT

*aa sequence (grey: CDR regions, IMGT numbering)* (SEQ ID NO:22)

QVQLVESGGGLVKPGGSLRLSCAASGFTFSDYYMYWVRQTPEKRLEWVAIISDGGYYTY
YADSIKGRFTISRDNAKNSLYLQMNSLRAEDTAVYYCTRGFPLLRHGAMDYWGQGTLVT
VSS

Fig. 2 hum A5-VH5

*nt sequence (coding strand)* (SEQ ID NO:23)

CAGGTTCAACTCGTTGAGAGCGGTGGCGGCCTTGTGAAACCGGGTGGCTCCCTGAG
GTTGAGCTGTGCGGCCTCAGGGTTCACCTTTAGTGACTACTACATGTACTGGGTCCG
GCAGGCCCCAGGCAAAGGCTTGGAGTGGGTTGCGATCATTAGCGACGGTGGGTACT
ATACATATTACGCCGATTCCGTCAAAGGGCGATTTACGATTAGTCGCGACAACGCGAA
AAACTCATTGTACCTTCAAATGAACTCTCTCAGAGCTGAAGATACTGCGGTGTACTAC
TGTACGAGGGGGTTTCCTTTGCTTAGGCACGGGGCCATGGACTATTGGGGCCAAGG
CACCCTCGTAACGGTTTCCTCT

*aa sequence (grey: CDR regions, IMGT numbering)* (SEQ ID NO:24)

QVQLVESGGGLVKPGGSLRLSCAASGFTFSDYYMYWVRQAPGKGLEWVAIISDGGYYT
YYADSVKGRFTISRDNAKNSLYLQMNSLRAEDTAVYYCTRGFPLLRHGAMDYWGQGTLV
TVSS

Fig. 3 nt and aa sequences of humanized VL chains of scFv A5

<u>hum A5-VL1</u>

*nt sequence (coding strand)* (SEQ ID NO:25)

GACATTCAAATGACCCAAAGCCCGAAATTCTTGTCTACCTCCGTTGGTGACAGAGTGA
CGATTACGTGTAGGGCTAGTCAGAACGTGGATACGAACTTGGCCTGGTATCAGCAGA
AGCCAGGACAGTCTCCAAAAGCCTTGATATATAGCGCAAGCTACCGATACTCCGATG
TTCCGGACCGATTTTCAGGGTCAGAGAGTGGCACAGATTTTACGCTTACAATTAGCAA
CCTGCAATCCGAGGACCTCGCCGAGTATTTCTGTCAACAATATGATTCCTATCCATAC
ACTTTTGGTGGGGGCACTAAACTTGAGATAAAG

*aa sequence (grey: CDR regions, IMGT numbering)* (SEQ ID NO:26)

DIQMTQSPKFLSTSVGDRVTITCRASQNVDTNLAWYQQKPGQSPKALIYSASYRYSDVPD
RFSGSESGTDFTLTISNLQSEDLAEYFCQQYDSYPYTFGGGTKLEIK

<u>hum A5-VL2</u>

*nt sequence (coding strand)* (SEQ ID NO:27)

GACATTCAGATGACGCAGAGCCCAAAGTTTTTGTCTACAAGTGTTGGTGATAGAGTCA
CTATCACGTGCAGGGCTTCTCAGAATGTAGACACTAACCTGGCCTGGTTCCAGCAGA
AGCCAGGAAAGGCTCCCAAATCACTCATCTACTCTGCATCATCCCTCTATTCTGACGT
GCCGGACCGATTCTCAGGCTCCGAGTCCGGCACCGACTTTACGTTGACGATCAGCAA
TCTTCAGCCGGAGGATTTTGCTGAATACTATTGTCAGCAGTACGATTCCTATCCATAC
ACATTCGGTGGGGGAACCAAGTTGGAAATAAAG

*aa sequence (grey: CDR regions, IMGT numbering)* (SEQ ID NO:28)

DIQMTQSPKFLSTSVGDRVTITCRASQNVDTNLAWFQQKPGKAPKSLIYSASSLYSDVPD
RFSGSESGTDFTLTISNLQPEDFAEYYCQQYDSYPYTFGGGTKLEIK

Fig. 4 hum A5-VL3

*nt sequence (coding strand)* (SEQ ID NO:29)

GACATTCAGATGACTCAGTCTCCCAGCTCATTGTCAGCTTCAGTAGGCGACCGAGTG
ACTATTACCTGTAGAGCATCTCAAAATGTGGATACAAACCTTGCATGGTTTCAGCAGA
AACCCGGAAAAGCCCCGAAAAGTTTGATTTACTCCGCCTCATCTCTCCAATCCGGCGT
GCCCAGCCGGTTTAGTGGCAGCGGAAGTGGGACTGACTTCACCCTCACGATCTCTAG
CCTTCAGCCAGAAGACTTCGCGACGTATTATTGCCAACAATACGATAGCTATCCATAT
ACGTTCGGGGGAGGCACCAAACTGGAGATAAAG

*aa sequence (grey: CDR regions, IMGT numbering)* (SEQ ID NO:30)

DIQMTQSPSSLSASVGDRVTITCRASQNVDTNLAWFQQKPGKAPKSLIYSASSLQSGVPS
RFSGSGSGTDFTLTISSLQPEDFATYYCQQYDSYPYTFGGGTKLEIK hum A5-VL4

*nt sequence (coding strand)* (SEQ ID NO:31)

GATATACAGATGACACAGTCTCCCAGCTCTATGAGTACCTCCGTTGGAGACCGGGTC
ACTGTAACATGCAGAGCCTCTCAAAACGTAGACACTAATGTAGCATGGTACCAGCAAA
AGCCTGGAAAAGCCCCGAAAGCGTTGATATATTCCGCTTCCTACAGATATTCTGGGGT
ACCAGATCGCTTCTCTGGCAGTGGAAGTGGGACCGACTTACTCTGACGATCAGCTC
CGTCCAGCCTGAAGATTTGGCTACTTACTTTGTCAGCAATATGACTCCTACCCATAC
ACATTCGGTGGGGGTACCAAATTGGAAATAAAG

*aa sequence (grey: CDR regions, IMGT numbering)* (SEQ ID NO:32)

DIQMTQSPSSMSTSVGDRVTVTCRASQNVDTNVAWYQQKPGKAPKALIYSASYRYSGVP
DRFSGSGSGTDFTLTISSVQPEDLATYFCQQYDSYPYTFGGGTKLEIK

Fig. 5 hum A5-VL5

*nt sequence (coding strand)* (SEQ ID NO:33)

GACATCCAAATGACACAATCACCTTCTAGCCTCTCAGCGTCAGTGGGCGATAGGGTT
ACTATTACTTGCCGCGCGAGCCAGAATGTTGATACGAATGTGGCCTGGTATCAGCAG
AAGCCGGGTAAGGCTCCGAAGGCACTGATTTATTCCGCCTCCTACCGATATTCCGGC
GTACCCGACAGGTTCAGTGGTTCCGGGTCAGGTACGGACTTTACGCTTACTATATCC
TCCCTGCAGCCTGAGGACGTAGCCACTTATTTTTGCCAGCAGTATGACAGTTACCCAT
ATACATTTGGTCAAGGTACAAAATTGGAGATCAAG

*aa sequence (grey: CDR regions, IMGT numbering)* (SEQ ID NO:34)

DIQMTQSPSSLSASVGDRVTITCRASQNVDTNVAWYQQKPGKAPKALIYSASYRYSGVP
DRFSGSGSGTDFTLTISSLQPEDVATYFCQQYDSYPYTFGQGTKLEIK hum A5-VL6

*nt sequence (coding strand)* (SEQ ID NO:35)

GATATACAGATGACGCAAAGTCCATCATCCCTCAGCGCAAGCGTGGGAGACAGAGTC
ACAATTACTTGCCGCGCGAGTCAGAACGTAGATACGAACCTGGCTTGGTATCAGCAG
AAACCGGGAAAGGCTCCCAAGTCACTGATCTACTCAGCCAGCTACCTGTATAGCGGT
GTTCCAAGTCGCTTTTCAGGTTCAGGCAGCGGCACTGACTTCACATTGACTATATCCT
CCCTTCAGCCCGAAGATGTCGCCACTTATTTTTGCCAACAATATGACTCCTATCCCTA
TACTTTCGGACAGGGGACCAAATTGGAGATAAAA

*aa sequence (grey: CDR regions, IMGT numbering)* (SEQ ID NO:36)

DIQMTQSPSSLSASVGDRVTITCRASQNVDTNLAWYQQKPGKAPKSLIYSASYLYSGVPS
RFSGSGSGTDFTLTISSLQPEDVATYFCQQYDSYPYTFGQGTKLEIK

Fig. 8C (SEQ ID NO: 40)
(SEQ ID NO: 38)
(SEQ ID NO: 44)

Fig. 8D

Fig. 9
A
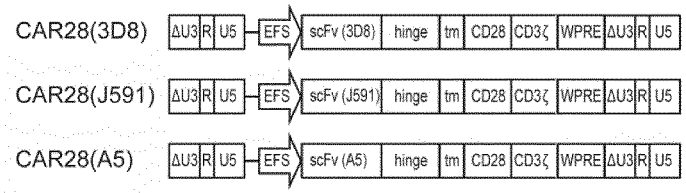
B
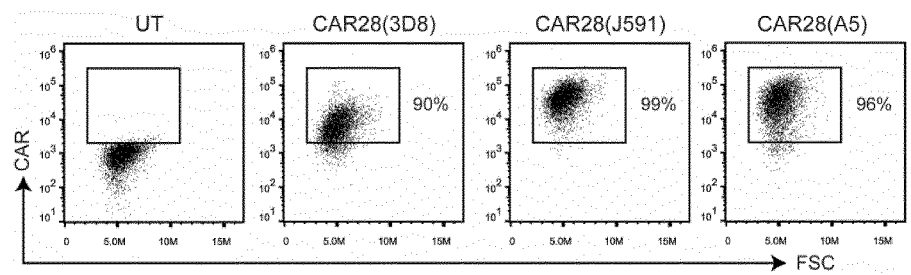
C
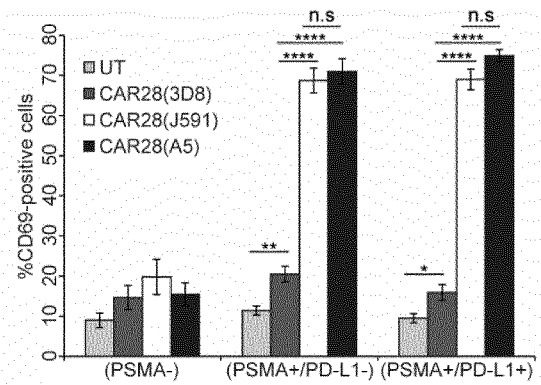
D
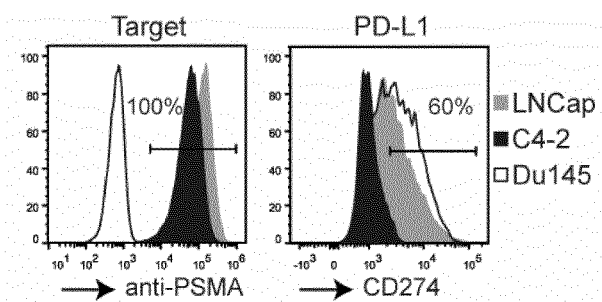

Fig. 11
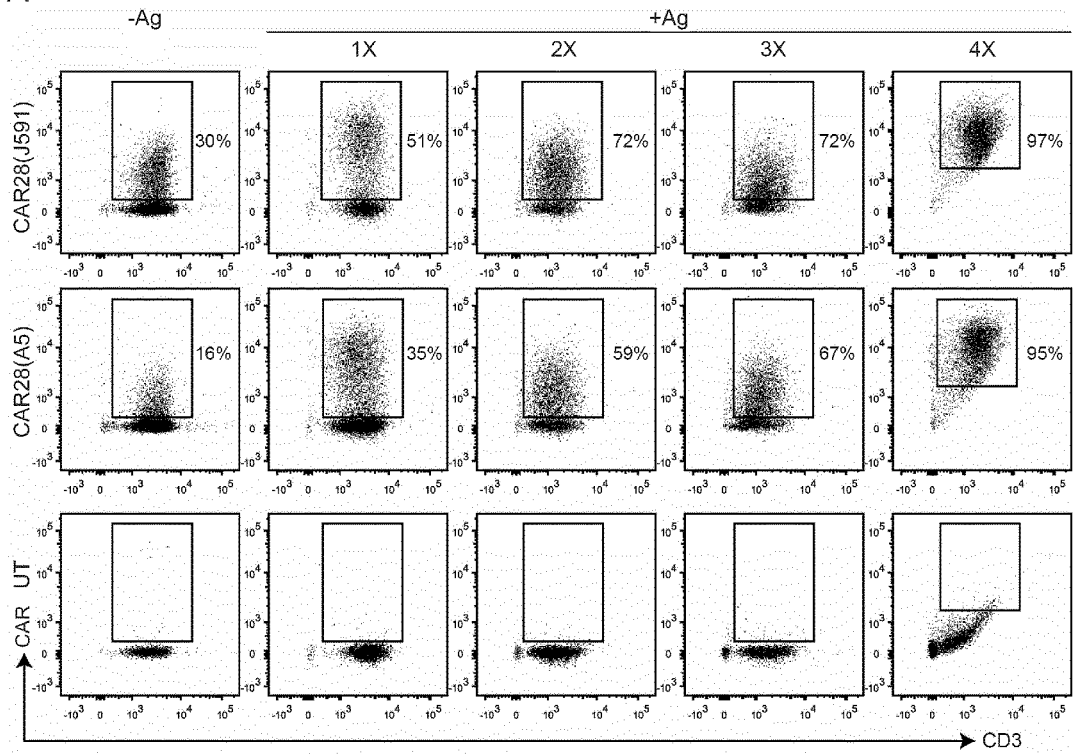
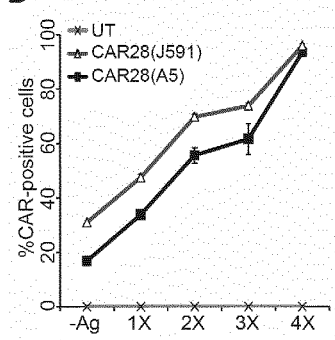
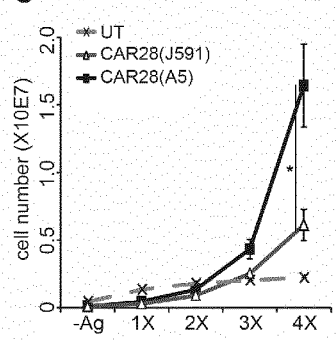
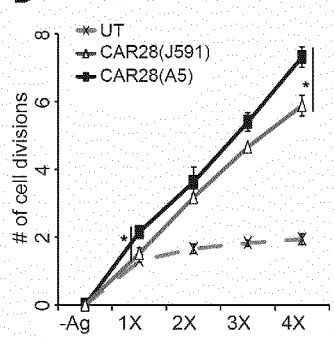
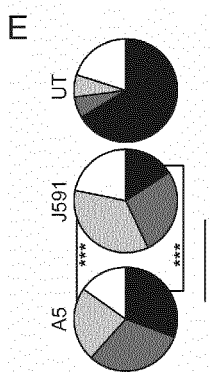
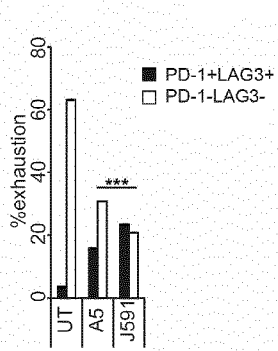

(SEQ ID NO: 37)
(SEQ ID NO: 39)
(SEQ ID NO: 43)

Fig. 13B

Fig. 14B (SEQ ID NO: 38)
(SEQ ID NO: 40)
(SEQ ID NO: 44)

SEQUENCE LISTING

```
<160> NUMBER OF SEQ ID NOS: 45

<210> SEQ ID NO 1
<211> LENGTH: 121
<212> TYPE: PRT
<213> ORGANISM: Mus musculus
<220> FEATURE:
<223> OTHER INFORMATION: murine sequence

<400> SEQUENCE: 1

Asp Val Lys Leu Val Glu Ser Gly Gly Gly Leu Val Lys Pro Gly Glu
1               5                   10                  15

Ser Leu Lys Leu Ser Cys Ile Ala Ser Gly Phe Thr Phe Ser Asp Tyr
            20                  25                  30
```

-continued

```
Tyr Met Tyr Trp Val Arg Gln Thr Pro Glu Lys Arg Leu Glu Trp Val
            35                  40                  45

Ala Ile Ile Ser Asp Gly Gly Tyr Tyr Thr Tyr Tyr Ser Asp Ile Ile
 50                  55                  60

Lys Gly Arg Phe Thr Ile Ser Arg Asp Asn Ala Lys Asn Asn Leu Tyr
 65                  70                  75                  80

Leu Gln Met Ser Ser Leu Lys Ser Glu Asp Thr Ala Met Tyr Tyr Cys
                85                  90                  95

Thr Arg Gly Phe Pro Leu Leu Arg His Gly Ala Met Asp Tyr Trp Gly
            100                 105                 110

Leu Gly Thr Ser Val Thr Val Ser Ser
        115                 120
```

<210> SEQ ID NO 2
<211> LENGTH: 9
<212> TYPE: PRT
<213> ORGANISM: artificial sequence
<220> FEATURE:
<223> OTHER INFORMATION: CDR - H1

<400> SEQUENCE: 2

```
Gly Phe Thr Phe Ser Asp Tyr Tyr Met
 1               5
```

<210> SEQ ID NO 3
<211> LENGTH: 7
<212> TYPE: PRT
<213> ORGANISM: artificial sequence
<220> FEATURE:
<223> OTHER INFORMATION: CDR-H2

<400> SEQUENCE: 3

```
Ile Ile Ser Asp Gly Gly Tyr
 1               5
```

<210> SEQ ID NO 4
<211> LENGTH: 12
<212> TYPE: PRT
<213> ORGANISM: artificial sequence
<220> FEATURE:
<223> OTHER INFORMATION: CDR-H3

<400> SEQUENCE: 4

```
Gly Phe Pro Leu Leu Arg His Gly Ala Met Asp Tyr
 1               5                  10
```

<210> SEQ ID NO 5
<211> LENGTH: 107
<212> TYPE: PRT
<213> ORGANISM: Mus musculus
<220> FEATURE:
<223> OTHER INFORMATION: murine sequence

<400> SEQUENCE: 5

```
Asp Ile Gln Met Thr Gln Ser Pro Lys Phe Met Ser Thr Ser Val Gly
 1               5                  10                  15

Asp Arg Val Ser Val Thr Cys Lys Ala Ser Gln Asn Val Asp Thr Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Asp Val Pro Asp Arg Phe Thr Gly
 50                  55                  60
```

-continued

Ser Glu Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asp Ser Tyr Pro Tyr
                85                  90                  95

Thr Phe Gly Gly Gly Thr Lys Leu Glu Ile Lys
            100                 105

<210> SEQ ID NO 6
<211> LENGTH: 11
<212> TYPE: PRT
<213> ORGANISM: artificial sequence
<220> FEATURE:
<223> OTHER INFORMATION: CDR-L1

<400> SEQUENCE: 6

Lys Ala Ser Gln Asn Val Asp Thr Asn Val Ala
1               5                   10

<210> SEQ ID NO 7
<211> LENGTH: 7
<212> TYPE: PRT
<213> ORGANISM: artificial sequence
<220> FEATURE:
<223> OTHER INFORMATION: CDR-L2

<400> SEQUENCE: 7

Ser Ala Ser Tyr Arg Tyr Ser
1               5

<210> SEQ ID NO 8
<211> LENGTH: 9
<212> TYPE: PRT
<213> ORGANISM: artificial sequence
<220> FEATURE:
<223> OTHER INFORMATION: CDR-L3

<400> SEQUENCE: 8

Gln Gln Tyr Asp Ser Tyr Pro Tyr Thr
1               5

<210> SEQ ID NO 9
<211> LENGTH: 8
<212> TYPE: PRT
<213> ORGANISM: artificial sequence
<220> FEATURE:
<223> OTHER INFORMATION: CDR-H1

<400> SEQUENCE: 9

Gly Phe Thr Phe Ser Asp Tyr Tyr
1               5

<210> SEQ ID NO 10
<211> LENGTH: 8
<212> TYPE: PRT
<213> ORGANISM: artificial sequence
<220> FEATURE:
<223> OTHER INFORMATION: CDR-H2

<400> SEQUENCE: 10

Ile Ser Asp Gly Gly Tyr Tyr Thr
1               5

<210> SEQ ID NO 11
<211> LENGTH: 16
<212> TYPE: PRT
<213> ORGANISM: artificial sequence

<220> FEATURE:
<223> OTHER INFORMATION: CDR-H3

<400> SEQUENCE: 11

Thr Arg Gly Phe Pro Leu Leu Arg His Gly Ala Met Asp Tyr Trp Gly
1               5                   10                  15

<210> SEQ ID NO 12
<211> LENGTH: 6
<212> TYPE: PRT
<213> ORGANISM: artificial sequence
<220> FEATURE:
<223> OTHER INFORMATION: CDR-L1 IMGT

<400> SEQUENCE: 12

Gln Asn Val Asp Thr Asn
1               5

<210> SEQ ID NO 13
<211> LENGTH: 3
<212> TYPE: PRT
<213> ORGANISM: artificial sequence
<220> FEATURE:
<223> OTHER INFORMATION: CDR-L2 IMGT

<400> SEQUENCE: 13

Ser Ala Ser
1

<210> SEQ ID NO 14
<211> LENGTH: 9
<212> TYPE: PRT
<213> ORGANISM: artificial sequence
<220> FEATURE:
<223> OTHER INFORMATION: CDR-L3 IMGT

<400> SEQUENCE: 14

Gln Gln Tyr Asp Ser Tyr Pro Tyr Thr
1               5

<210> SEQ ID NO 15
<211> LENGTH: 363
<212> TYPE: DNA
<213> ORGANISM: artificial sequence
<220> FEATURE:
<223> OTHER INFORMATION: hum-A5-VH1 coding strand

<400> SEQUENCE: 15
gacgtgaaac tcgtggaatc aggcggtggg ttggttaaac cgggtgaatc cctccgcctc      60
tcttgcgcgg cgagcgggtt cacatttca gattattata tgtattggat ccgacaaact      120
cctgaaaaac ggcttgaatg ggttgccatt atttcagatg gcggatatta cacttactat      180
tctgacattg tgaaaggtcg ctttacaatc tccagggaca atgcgaaaaa caacctgtac      240
ttgcaaatgt ctagcctgcg atcagaggat actgcaatgt actactgcac cgcggatttt      300
ccgcttctgc gacatggagc tatggactac tggggtctcg gcacgagtgt aacggtgagt      360
agt                                                                   363

<210> SEQ ID NO 16
<211> LENGTH: 121
<212> TYPE: PRT
<213> ORGANISM: artificial sequence
<220> FEATURE:
<223> OTHER INFORMATION: hum A5- VH1

<400> SEQUENCE: 16

Asp Val Lys Leu Val Glu Ser Gly Gly Gly Leu Val Lys Pro Gly Glu
1               5                   10                  15

Ser Leu Arg Leu Ser Cys Ala Ala Ser Gly Phe Thr Phe Ser Asp Tyr
            20                  25                  30

Tyr Met Tyr Trp Ile Arg Gln Thr Pro Glu Lys Arg Leu Glu Trp Val
        35                  40                  45

Ala Ile Ile Ser Asp Gly Gly Tyr Tyr Thr Tyr Tyr Ser Asp Ile Val
    50                  55                  60

Lys Gly Arg Phe Thr Ile Ser Arg Asp Asn Ala Lys Asn Asn Leu Tyr
65                  70                  75                  80

Leu Gln Met Ser Ser Leu Arg Ser Glu Asp Thr Ala Met Tyr Tyr Cys
                85                  90                  95

Thr Arg Gly Phe Pro Leu Leu Arg His Gly Ala Met Asp Tyr Trp Gly
            100                 105                 110

Leu Gly Thr Ser Val Thr Val Ser Ser
            115                 120

<210> SEQ ID NO 17
<211> LENGTH: 363
<212> TYPE: DNA
<213> ORGANISM: artificial sequence
<220> FEATURE:
<223> OTHER INFORMATION: hum A5 VH2 coding strand

<400> SEQUENCE: 17
caagtccaac tggtggaatc tggtggtggt cttgttaaac caggggaaag tctgcgactg      60
agctgcgccg cgagtgggtt cacgttttcc gactactata tgagctggat tagacagacg     120
cctgagaaac gactcgagtg ggttagtatt attagtgatg agggtattta cacctactat     180
gcagatatcg ttaaagggcg atttactatc agccgagata acgcaaaaaa caacttgtat     240
ctccaaatgt cctcactgcg ggctgaggat accgctgtat attactgtac caggggtttt     300
cctctcctgc ggcacggggc tatggattat tggggtttgg ggacctcagt tacggtatca     360
tcc                                                                    363

<210> SEQ ID NO 18
<211> LENGTH: 121
<212> TYPE: PRT
<213> ORGANISM: artificial sequence
<220> FEATURE:
<223> OTHER INFORMATION: hum A5 VH2

<400> SEQUENCE: 18

Gln Val Gln Leu Val Glu Ser Gly Gly Gly Leu Val Lys Pro Gly Glu
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Thr Pro Glu Lys Arg Leu Glu Trp Val
        35                  40                  45

Ser Ile Ile Ser Asp Gly Gly Tyr Tyr Thr Tyr Tyr Ala Asp Ile Val
    50                  55                  60

Lys Gly Arg Phe Thr Ile Ser Arg Asp Asn Ala Lys Asn Asn Leu Tyr
65                  70                  75                  80

Leu Gln Met Ser Ser Leu Arg Ala Glu Asp Thr Ala Val Tyr Tyr Cys
                85                  90                  95

Thr Arg Gly Phe Pro Leu Leu Arg His Gly Ala Met Asp Tyr Trp Gly

```
                   100                 105                 110

Leu Gly Thr Ser Val Thr Val Ser Ser
        115                 120

<210> SEQ ID NO 19
<211> LENGTH: 363
<212> TYPE: DNA
<213> ORGANISM: artificial sequence
<220> FEATURE:
<223> OTHER INFORMATION: hum A5 VH3 coding strand

<400> SEQUENCE: 19
caggtacaac tggtggaaag cgggggagga cttgtcaagc ccggagggtc cctcagattg      60
agctgtgcgg cctccgggtt cacctttttcc gattactata tgtcctggat tcggcaggca    120
ccgggtaagg gattggagtg gtatcttat ataagcgacg ggggctatta tacttattac     180
gctgatagtg tgaaagggcg cttcactatc agccgagaca atgcgaagaa ttctttgtat    240
ttgcagatga attctttgag agccgaggat acagcggttt attactgtac gagagggttt    300
ccacttctga ggcatggtgc gatggattat tggggactgg gtactagcgt caccgtaagc    360
tct                                                                   363

<210> SEQ ID NO 20
<211> LENGTH: 121
<212> TYPE: PRT
<213> ORGANISM: artificial sequence
<220> FEATURE:
<223> OTHER INFORMATION: hum A5 VH3

<400> SEQUENCE: 20

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Asp Gly Gly Tyr Tyr Thr Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Thr Arg Gly Phe Pro Leu Leu Arg His Gly Ala Met Asp Tyr Trp Gly
            100                 105                 110

Leu Gly Thr Ser Val Thr Val Ser Ser
        115                 120

<210> SEQ ID NO 21
<211> LENGTH: 363
<212> TYPE: DNA
<213> ORGANISM: artificial sequence
<220> FEATURE:
<223> OTHER INFORMATION: hum A5 VH4

<400> SEQUENCE: 21
caagtacagt tggttgaaag tggtggcggc ctcgttaagc ctggcggatc tctgagattg      60
tcttgtgctg cgtctggatt cactttttcc gactattata tgtattgggt gagacagaca    120
ccagaaaaaa ggcttgaatg ggtcgccata atatccgatg gggttatta tacttactac    180
```

```
gctgacagca taaaagggag attcacgata agccgggata atgccaaaaa tagtctttat    240
ctccaaatga actctctgag agcggaagat actgctgtat actattgcac tagagggttc    300
ccattgttga catggagc aatggattac tggggcaag ggactctcgt aaccgtctca       360
tct                                                                  363
```

<210> SEQ ID NO 22
<211> LENGTH: 121
<212> TYPE: PRT
<213> ORGANISM: artificial sequence
<220> FEATURE:
<223> OTHER INFORMATION: hum A5 VH4

<400> SEQUENCE: 22

```
Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Tyr Trp Val Arg Gln Thr Pro Glu Lys Arg Leu Glu Trp Val
        35                  40                  45

Ala Ile Ile Ser Asp Gly Gly Tyr Tyr Thr Tyr Tyr Ala Asp Ser Ile
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Thr Arg Gly Phe Pro Leu Leu Arg His Gly Ala Met Asp Tyr Trp Gly
            100                 105                 110

Gln Gly Thr Leu Val Thr Val Ser Ser
        115                 120
```

<210> SEQ ID NO 23
<211> LENGTH: 363
<212> TYPE: DNA
<213> ORGANISM: artificial sequence
<220> FEATURE:
<223> OTHER INFORMATION: hum A5 VH5 coding strand

<400> SEQUENCE: 23

```
caggttcaac tcgttgagag cggtggcggc cttgtgaaac cgggtggctc cctgaggttg     60
agctgtgcgg cctcagggtt cacctttagt gactactaca tgtactgggt ccggcaggcc    120
ccaggcaaag gcttggagtg ggttgcgatc attagcgacg gtggtgtacta tacatattac   180 gccgattccg tcaaagggcg atttacgatt agtcgcgaca cgcgaaaaa ctcattgtac     240 cttcaaatga actctctcag agctgaagat actgcggtgt actactgtac gagggggttt    300
cctttgctta ggcacggggc catggactat tgggccaag gcaccctcgt aacggtttcc    360
tct                                                                  363
```

<210> SEQ ID NO 24
<211> LENGTH: 121
<212> TYPE: PRT
<213> ORGANISM: artificial sequence
<220> FEATURE:
<223> OTHER INFORMATION: hum A5 VH5

<400> SEQUENCE: 24

```
Gln Val Gln Leu Val Glu Ser Gly Gly Gly Leu Val Lys Pro Gly Gly
1               5                   10                  15
```

```
Ser Leu Arg Leu Ser Cys Ala Ala Ser Gly Phe Thr Phe Ser Asp Tyr
         20                  25                  30

Tyr Met Tyr Trp Val Arg Gln Ala Pro Gly Lys Gly Leu Glu Trp Val
         35                  40                  45

Ala Ile Ile Ser Asp Gly Gly Tyr Tyr Thr Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
             85                  90                  95

Thr Arg Gly Phe Pro Leu Leu Arg His Gly Ala Met Asp Tyr Trp Gly
            100                 105                 110

Gln Gly Thr Leu Val Thr Val Ser Ser
            115                 120
```

<210> SEQ ID NO 25
<211> LENGTH: 321
<212> TYPE: DNA
<213> ORGANISM: artificial sequence
<220> FEATURE:
<223> OTHER INFORMATION: hum A5 VL1

<400> SEQUENCE: 25

```
gacattcaaa tgacccaaag cccgaaattc ttgtctacct ccgttggtga cagagtgacg      60
attacgtgta gggctagtca gaacgtggat acgaacttgg cctggtatca gcagaagcca     120
ggacagtctc caaaagcctt gatatatagc gcaagctacc gatactccga tgttccggac     180
cgatttcag ggtcagagag tggcacagat tttacgctta caattagcaa cctgcaatcc      240
gaggaccctcg ccgagtattt ctgtcaacaa tatgattcct atccatacac ttttggtggg    300
ggcactaaac ttgagataaa g                                                321
```

<210> SEQ ID NO 26
<211> LENGTH: 107
<212> TYPE: PRT
<213> ORGANISM: artificial sequence
<220> FEATURE:
<223> OTHER INFORMATION: hum A5 VL1

<400> SEQUENCE: 26

```
Asp Ile Gln Met Thr Gln Ser Pro Lys Phe Leu Ser Thr Ser Val Gly
 1               5                  10                  15

Asp Arg Val Thr Ile Thr Cys Arg Ala Ser Gln Asn Val Asp Thr Asn
             20                  25                  30

Leu Ala Trp Tyr Gln Gln Lys Pro Gly Gln Ser Pro Lys Ala Leu Ile
         35                  40                  45

Tyr Ser Ala Ser Tyr Arg Tyr Ser Asp Val Pro Asp Arg Phe Ser Gly
 50                  55                  60

Ser Glu Ser Gly Thr Asp Phe Thr Leu Thr Ile Ser Asn Leu Gln Ser
 65                  70                  75                  80

Glu Asp Leu Ala Glu Tyr Phe Cys Gln Gln Tyr Asp Ser Tyr Pro Tyr
             85                  90                  95

Thr Phe Gly Gly Gly Thr Lys Leu Glu Ile Lys
            100                 105
```

<210> SEQ ID NO 27
<211> LENGTH: 321
<212> TYPE: DNA
<213> ORGANISM: artificial sequence

```
<220> FEATURE:
<223> OTHER INFORMATION: hum A5 VL2 coding strand

<400> SEQUENCE: 27
gacattcaga tgacgcagag cccaaagttt tgtctacaa gtgttggtga tagagtcact      60
atcacgtgca gggcttctca gaatgtagac actaacctgg cctggttcca gcagaagcca    120
ggaaaggctc ccaaatcact catctactct gcatcatccc tctattctga cgtgccggac    180
cgattctcag gctccgagtc cggcaccgac tttacgttga cgatcagcaa tcttcagccg    240
gaggattttg ctgaatacta ttgtcagcag tacgattcct atccatacac attcggtggg    300
ggaaccaagt tggaaataaa g                                              321

<210> SEQ ID NO 28
<211> LENGTH: 107
<212> TYPE: PRT
<213> ORGANISM: artificial sequence
<220> FEATURE:
<223> OTHER INFORMATION: hum A5 VL2

<400> SEQUENCE: 28

Asp Ile Gln Met Thr Gln Ser Pro Lys Phe Leu Ser Thr Ser Val Gly
1               5                   10                  15

Asp Arg Val Thr Ile Thr Cys Arg Ala Ser Gln Asn Val Asp Thr Asn
            20                  25                  30

Leu Ala Trp Phe Gln Gln Lys Pro Gly Lys Ala Pro Lys Ser Leu Ile
        35                  40                  45

Tyr Ser Ala Ser Ser Leu Tyr Ser Asp Val Pro Asp Arg Phe Ser Gly
    50                  55                  60

Ser Glu Ser Gly Thr Asp Phe Thr Leu Thr Ile Ser Asn Leu Gln Pro
65                  70                  75                  80

Glu Asp Phe Ala Glu Tyr Tyr Cys Gln Gln Tyr Asp Ser Tyr Pro Tyr
                85                  90                  95

Thr Phe Gly Gly Gly Thr Lys Leu Glu Ile Lys
            100                 105

<210> SEQ ID NO 29
<211> LENGTH: 321
<212> TYPE: DNA
<213> ORGANISM: artificial sequence
<220> FEATURE:
<223> OTHER INFORMATION: hum A5 VL3

<400> SEQUENCE: 29
gacattcaga tgactcagtc tcccagctca ttgtcagctt cagtaggcga ccgagtgact      60
attacctgta gagcatctca aaatgtggat acaaaccttg catggtttca gcagaaaccc    120
ggaaaagccc cgaaaagttt gatttactcc gcctcatctc tccaatccgg cgtgcccagc    180
cggtttagtg gcagcggaag tgggactgac ttcaccctca cgatctctag ccttcagcca    240
gaagacttcg cgacgtatta ttgccaacaa tacgatagct atccatatac gttcggggga    300
ggcaccaaac tggagataaa g                                              321

<210> SEQ ID NO 30
<211> LENGTH: 107
<212> TYPE: PRT
<213> ORGANISM: artificial sequence
<220> FEATURE:
<223> OTHER INFORMATION: hum A5 VL3

<400> SEQUENCE: 30
```

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Val Asp Thr Asn
            20                  25                  30

Leu Ala Trp Phe Gln Lys Pro Gly Lys Ala Pro Lys Ser Leu Ile
        35                  40                  45

Tyr Ser Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asp Ser Tyr Pro Tyr
                85                  90                  95

Thr Phe Gly Gly Gly Thr Lys Leu Glu Ile Lys
            100                 105
```

<210> SEQ ID NO 31
<211> LENGTH: 321
<212> TYPE: DNA
<213> ORGANISM: artificial sequence
<220> FEATURE:
<223> OTHER INFORMATION: hum A5 VL4

<400> SEQUENCE: 31

```
gatatacaga tgacacagtc tcccagctct atgagtacct ccgttggaga ccgggtcact    60
gtaacatgca gagcctctca aaacgtagac actaatgtag catggtacca gcaaaagcct   120
ggaaaagccc cgaaagcgtt gatatattcc gcttcctaca gatattctgg ggtaccagat   180
cgcttctctg gcagtggaag tgggaccgac tttactctga cgatcagctc cgtccagcct   240
gaagatttgg ctacttactt ttgtcagcaa tatgactcct acccatacac attcggtggg   300
ggtaccaaat tggaaataaa g                                              321
```

<210> SEQ ID NO 32
<211> LENGTH: 107
<212> TYPE: PRT
<213> ORGANISM: artificial sequence
<220> FEATURE:
<223> OTHER INFORMATION: hum A5 VL4

<400> SEQUENCE: 32

```
Asp Ile Gln Met Thr Gln Ser Pro Ser Ser Met Ser Thr Ser Val Gly
1               5                   10                  15

Asp Arg Val Thr Val Thr Cys Arg Ala Ser Gln Asn Val Asp Thr Asn
            20                  25                  30

Val Ala Trp Tyr Gln Gln Lys Pro Gly Lys Ala Pro Lys Ala Leu Ile
        35                  40                  45

Tyr Ser Ala Ser Tyr Arg Tyr Ser Gly Val Pro Asp Arg Phe Ser Gly
50                  55                  60

Ser Gly Ser Gly Thr Asp Phe Thr Leu Thr Ile Ser Ser Val Gln Pro
65                  70                  75                  80

Glu Asp Leu Ala Thr Tyr Phe Cys Gln Gln Tyr Asp Ser Tyr Pro Tyr
                85                  90                  95

Thr Phe Gly Gly Gly Thr Lys Leu Glu Ile Lys
            100                 105
```

<210> SEQ ID NO 33
<211> LENGTH: 321
<212> TYPE: DNA

<213> ORGANISM: artificial sequence
<220> FEATURE:
<223> OTHER INFORMATION: hum A5 VL5

<400> SEQUENCE: 33

```
gacatccaaa tgacacaatc accttctagc ctctcagcgt cagtgggcga tagggttact    60
attacttgcc gcgcgagcca gaatgttgat acgaatgtgg cctggtatca gcagaagccg   120
ggtaaggctc cgaaggcact gatttattcc gcctcctacc gatattccgg cgtacccgac   180
aggttcagtg gttccgggtc aggtacggac tttacgctta ctatatcctc cctgcagcct   240
gaggacgtag ccacttattt ttgccagcag tatgacagtt acccatatac atttggtcaa   300
ggtacaaaat tggagatcaa g                                             321
```

<210> SEQ ID NO 34
<211> LENGTH: 107
<212> TYPE: PRT
<213> ORGANISM: artificial sequence
<220> FEATURE:
<223> OTHER INFORMATION: hum A5 VL5

<400> SEQUENCE: 34

```
Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Asn Val Asp Thr Asn
            20                  25                  30
Val Ala Trp Tyr Gln Gln Lys Pro Gly Lys Ala Pro Lys Ala Leu Ile
        35                  40                  45
Tyr Ser Ala Ser Tyr Arg Tyr Ser Gly Val Pro Asp Arg Phe Ser Gly
    50                  55                  60
Ser Gly Ser Gly Thr Asp Phe Thr Leu Thr Ile Ser Ser Leu Gln Pro
65                  70                  75                  80
Glu Asp Val Ala Thr Tyr Phe Cys Gln Gln Tyr Asp Ser Tyr Pro Tyr
                85                  90                  95
Thr Phe Gly Gln Gly Thr Lys Leu Glu Ile Lys
            100                 105
```

<210> SEQ ID NO 35
<211> LENGTH: 321
<212> TYPE: DNA
<213> ORGANISM: artificial sequence
<220> FEATURE:
<223> OTHER INFORMATION: hum A5 - VL6

<400> SEQUENCE: 35

```
gatatacaga tgacgcaaag tccatcatcc ctcagcgcaa gcgtgggaga cagagtcaca    60
attacttgcc gcgcgagtca gaacgtagat acgaacctgg cttggtatca gcagaaaccg   120
ggaaaggctc ccaagtcact gatctactca gccagctacc tgtatagcgg tgttccaagt   180
cgcttttcag gttcaggcag cggcactgac ttcacattga ctatatcctc ccttcagccc   240
gaagatgtcg ccacttattt ttgccaacaa tatgactcct atccctatac tttcggacag   300
gggaccaaat tggagataaa a                                             321
```

<210> SEQ ID NO 36
<211> LENGTH: 107
<212> TYPE: PRT
<213> ORGANISM: artificial sequence
<220> FEATURE:
<223> OTHER INFORMATION: hum A5- VL6

<400> SEQUENCE: 36

Asp Ile Gln Met Thr Gln Ser Pro Ser Leu Ser Ala Ser Val Gly
1               5                   10                  15

Asp Arg Val Thr Ile Thr Cys Arg Ala Ser Gln Asn Val Asp Thr Asn
            20                  25                  30

Leu Ala Trp Tyr Gln Gln Lys Pro Gly Lys Ala Pro Lys Ser Leu Ile
        35                  40                  45

Tyr Ser Ala Ser Tyr Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Phe Cys Gln Gln Tyr Asp Ser Tyr Pro Tyr
                85                  90                  95

Thr Phe Gly Gln Gly Thr Lys Leu Glu Ile Lys
            100                 105

<210> SEQ ID NO 37
<211> LENGTH: 2055
<212> TYPE: DNA
<213> ORGANISM: artificial sequence
<220> FEATURE:
<223> OTHER INFORMATION: A5CAR28, coding strand

<400> SEQUENCE: 37

| | |
|---|---|
| atggattttc aggtgcagat tttcagcttc ctgctaatca gtgcctcagt cataatgtct | 60 |
| agagacgtta agttggtgga gagtggagga ggtttggtaa aaccaggaga atcccttaaa | 120 |
| ctctcttgca ttgcctcagg ctttaccttt tccgattatt atatgtattg ggtccgacaa | 180 |
| acacccgaaa aacgattgga atgggttgca attatatctg acggtggcta ctacacatat | 240 |
| tattctgata ttatcaaggg tagatttact atctccaggg ataatgccaa aaataatctc | 300 |
| taccttcaga tgtcttccct caaaagtgaa gatacggcca tgtattattg cacacgcggt | 360 |
| tttccattgc ttaggcacgg ggcaatggat tactgggac ttggtacctc cgtcacggta | 420 |
| agttctggcg gtggcggaag tggaggcggg ggttctggtg gtgggggtc tgacatccag | 480 |
| atgactcaaa gccctaaatt catgagcacg tcagttggga tcgagtctc cgttacgtgt | 540 |
| aaggcttctc aaaatgtaga cactaacgtc gcatggtacc aacagaagcc aggccagtct | 600 |
| ccgaaagccc tgatctacag cgcttcatac aggtattctg acgtacccga ccgattcact | 660 |
| ggatcagaga gtggaactga ctttacccett accatcagca acgtacaatc gaggatctc | 720 |
| gcagaatatt tttgccaaca gtacgattcc tatccatata ctttcggcgg aggcacgaag | 780 |
| cttgaaatca gtcggatcc cgccgagccc aaatctcctg acaaaactca cacatgccca | 840 |
| ccgtgcccag cacctccagt cgcgggaccg tcagtcttcc tcttccccc aaaacccaag | 900 |
| gacaccctca tgatcgcccg gacccctgag gtcacatgcg tggtggtgga cgtgagccac | 960 |
| gaagaccctg aggtcaagtt caactggtac gtggacggcg tggaggtgca taatgccaag | 1020 |
| acaaagccgc gggaggagca gtacaacagc acgtaccgtg tggtcagcgt cctcaccgtc | 1080 |
| ctgcaccagg actggctgaa tggcaaggag tacaagtgca aggtctccaa caaagccctc | 1140 |
| ccagccccca tcgagaaaac catctccaaa gccaaggc agccccgaga accacaggtg | 1200 |
| tacaccctgc ccccatcccg ggatgagctg accaagaacc aggtcagcct gacctgcctg | 1260 |
| gtcaaaggct tctatcccag cgacatcgcc gtggagtggg agagcaatgg gcagccggag | 1320 |
| aacaactaca agaccacgcc tcccgtgctg gactccgacg gctccttctt cctctacagc | 1380 |

| | |
|---|---|
| aagctcaccg tggacaagag caggtggcag caggggaacg tcttctcatg ctccgtgatg | 1440 |
| catgaggctc tgcacaacca ctacacgcag aagagcctct ccctgtctcc gggtaaaaaa | 1500 |
| gatcccaaat tttgggtgct ggtggtggtt ggtggagtcc tggcttgcta tagcttgcta | 1560 |
| gtaacagtgg cctttattat tttctgggtg aggagtaaga ggagcaggct cctgcacagt | 1620 |
| gactacatga acatgactcc ccgccgcccc gggcccaccc gcaagcatta ccaggcctat | 1680 |
| gccgccgcac gcgacttcgc agcctatcgc tccctgagag tgaagttcag caggagcgca | 1740 |
| gacgcccccg cgtaccagca gggccagaac cagctctata cgagctcaa tctaggacga | 1800 |
| agagaggagt acgatgtttt ggacaagaga cgtggccggg accctgagat gggggggaaag | 1860 |
| ccgagaagga agaaccctca ggaaggcctg tacaatgaac tgcagaaaga taagatggcg | 1920 |
| gaggcctaca gtgagattgg gatgaaaggc gagcgccgga ggggcaaggg gcacgatggc | 1980 |
| ctttaccagg gtctcagtac agccaccaag gacacctacg acgcccttca catgcaggcc | 2040 |
| ctgccccctc gctaa | 2055 |

```
<210> SEQ ID NO 38
<211> LENGTH: 2043
<212> TYPE: DNA
<213> ORGANISM: artificial sequence
<220> FEATURE:
<223> OTHER INFORMATION: A5CAR41,coding strand

<400> SEQUENCE: 38
```

| | |
|---|---|
| atggattttc aggtgcagat tttcagcttc tgctaatca gtgcctcagt cataatgtct | 60 |
| agagacgtta agttggtgga gagtggagga ggtttggtaa accaggaga atcccttaaa | 120 |
| ctctcttgca ttgcctcagg ctttaccttt tccgattatt atatgtattg ggtccgacaa | 180 |
| acacccgaaa aacgattgga atgggttgca attatatctg acggtggcta ctacacatat | 240 |
| tattctgata ttatcaaggg tagatttact atctccaggg ataatgccaa aaataatctc | 300 |
| taccttcaga tgtcttccct caaaagtgaa gatacggcca tgtattattg cacacgcggt | 360 |
| tttccattgc ttaggcacgg ggcaatggat tactggggac ttggtacctc cgtcacggta | 420 |
| agttctggcg gtggcggaag tggaggcggg ggttctggtg gtgggggggtc tgacatccag | 480 |
| atgactcaaa gccctaaatt catgagcacg tcagttggag atcgagtctc cgttacgtgt | 540 |
| aaggcttctc aaaatgtaga cactaacgtc gcatggtacc aacagaagcc aggccagtct | 600 |
| ccgaaagccc tgatctacag cgcttcatac aggtattctg acgtacccga ccgattcact | 660 |
| ggatcagaga gtgaactga ctttacccctt accatcagca acgtacaatc cgaggatctc | 720 |
| gcagaatatt tttgccaaca gtacgattcc tatccatata ctttcggcgg aggcacgaag | 780 |
| cttgaaatca gtcggatcc cgccgagccc aaatctcctg acaaaactca cacatgccca | 840 |
| ccgtgcccag cacctccagt cgcgggaccg tcagtcttcc tcttccccc aaaacccaag | 900 |
| gacaccctca tgatcgcccg gacccctgag gtcacatgcg tggtggtgga cgtgagccac | 960 |
| gaagaccctg aggtcaagtt caactggtac gtggacggcg tggaggtgca taatgccaag | 1020 |
| acaaagccgc gggaggagca gtacaacagc acgtaccgtg tggtcagcgt cctcaccgtc | 1080 |
| ctgcaccagg actggctgaa tggcaaggag tacaagtgca aggtctccaa caaagccctc | 1140 |
| ccagccccca tcgagaaaac catctccaaa gccaagggc agccccgaga accacaggtg | 1200 |
| tacaccctgc ccccatcccg ggatgagctg accaagaacc aggtcagcct gacctgcctg | 1260 |
| gtcaaaggct tctatcccag cgacatcgcc gtggagtggg agagcaatgg gcagccggag | 1320 |
| aacaactaca agaccacgcc tcccgtgctg gactccgacg gctccttctt cctctacagc | 1380 |

```
aagctcaccg tggacaagag caggtggcag caggggaacg tcttctcatg ctccgtgatg    1440
catgaggctc tgcacaacca ctacacgcag aagagcctct cgagcctgtc tccgggtaaa    1500
aaaatctaca tctgggcgcc cttggccggg acttgtgggg tccttctcct gtcactggtt    1560
atcacccttt actgcaaacg gggcagaaag aaactcctgt atatattcaa acaaccattt    1620
atgagaccag tacaaactac tcaagaggaa gatggctgta gctgccgatt tccagaagaa    1680
gaagaaggag gatgtgaact gctgagagtg aagttcagca ggagcgcaga cgcccccgcg    1740
taccagcagg gccagaacca gctctataac gagctcaatc taggacgaag agaggagtac    1800
gatgttttgg acaagagacg tggccggac cctgagatgg ggggaaagcc gagaaggaag    1860
aaccctcagg aaggcctgta caatgaactg cagaaagata gatggcgga ggcctacagt    1920 gagattggga tgaaaggcga gcgccggagg ggcaaggggc acgatggcct ttaccagggt    1980
ctcagtacag ccaccaagga cacctacgac gcccttcaca tgcaggccct gccccctcgc    2040
taa                                                                  2043
```

<210> SEQ ID NO 39
<211> LENGTH: 684
<212> TYPE: PRT
<213> ORGANISM: artificial sequence
<220> FEATURE:
<223> OTHER INFORMATION: A5CAR28

<400> SEQUENCE: 39

```
Met Asp Phe Gln Val Gln Ile Phe Ser Phe Leu Leu Ile Ser Ala Ser
1               5                   10                  15

Val Ile Met Ser Arg Asp Val Lys Leu Val Glu Ser Gly Gly Gly Leu
            20                  25                  30

Val Lys Pro Gly Glu Ser Leu Lys Leu Ser Cys Ile Ala Ser Gly Phe
        35                  40                  45

Thr Phe Ser Asp Tyr Tyr Met Tyr Trp Val Arg Gln Thr Pro Glu Lys
    50                  55                  60

Arg Leu Glu Trp Val Ala Ile Ile Ser Asp Gly Gly Tyr Tyr Thr Tyr
65                  70                  75                  80

Tyr Ser Asp Ile Ile Lys Gly Arg Phe Thr Ile Ser Arg Asp Asn Ala
                85                  90                  95

Lys Asn Asn Leu Tyr Leu Gln Met Ser Ser Leu Lys Ser Glu Asp Thr
            100                 105                 110

Ala Met Tyr Tyr Cys Thr Arg Gly Phe Pro Leu Leu Arg His Gly Ala
        115                 120                 125

Met Asp Tyr Trp Gly Leu Gly Thr Ser Val Thr Val Ser Ser Gly Gly
    130                 135                 140

Gly Gly Ser Gly Gly Gly Gly Ser Gly Gly Gly Gly Ser Asp Ile Gln
145                 150                 155                 160

Met Thr Gln Ser Pro Lys Phe Met Ser Thr Ser Val Gly Asp Arg Val
                165                 170                 175

Ser Val Thr Cys Lys Ala Ser Gln Asn Val Asp Thr Asn Val Ala Trp
            180                 185                 190

Tyr Gln Gln Lys Pro Gly Gln Ser Pro Lys Ala Leu Ile Tyr Ser Ala
        195                 200                 205

Ser Tyr Arg Tyr Ser Asp Val Pro Asp Arg Phe Thr Gly Ser Glu Ser
    210                 215                 220

Gly Thr Asp Phe Thr Leu Thr Ile Ser Asn Val Gln Ser Glu Asp Leu
225                 230                 235                 240
```

```
Ala Glu Tyr Phe Cys Gln Gln Tyr Asp Ser Tyr Pro Tyr Thr Phe Gly
                245                 250                 255

Gly Gly Thr Lys Leu Glu Ile Lys Ser Asp Pro Ala Glu Pro Lys Ser
            260                 265                 270

Pro Asp Lys Thr His Thr Cys Pro Pro Cys Pro Ala Pro Pro Val Ala
        275                 280                 285

Gly Pro Ser Val Phe Leu Phe Pro Pro Lys Pro Lys Asp Thr Leu Met
    290                 295                 300

Ile Ala Arg Thr Pro Glu Val Thr Cys Val Val Val Asp Val Ser His
305                 310                 315                 320

Glu Asp Pro Glu Val Lys Phe Asn Trp Tyr Val Asp Gly Val Glu Val
                325                 330                 335

His Asn Ala Lys Thr Lys Pro Arg Glu Glu Gln Tyr Asn Ser Thr Tyr
            340                 345                 350

Arg Val Val Ser Val Leu Thr Val Leu His Gln Asp Trp Leu Asn Gly
        355                 360                 365

Lys Glu Tyr Lys Cys Lys Val Ser Asn Lys Ala Leu Pro Ala Pro Ile
    370                 375                 380

Glu Lys Thr Ile Ser Lys Ala Lys Gly Gln Pro Arg Glu Pro Gln Val
385                 390                 395                 400

Tyr Thr Leu Pro Pro Ser Arg Asp Glu Leu Thr Lys Asn Gln Val Ser
                405                 410                 415

Leu Thr Cys Leu Val Lys Gly Phe Tyr Pro Ser Asp Ile Ala Val Glu
            420                 425                 430

Trp Glu Ser Asn Gly Gln Pro Glu Asn Asn Tyr Lys Thr Thr Pro Pro
        435                 440                 445

Val Leu Asp Ser Asp Gly Ser Phe Phe Leu Tyr Ser Lys Leu Thr Val
    450                 455                 460

Asp Lys Ser Arg Trp Gln Gln Gly Asn Val Phe Ser Cys Ser Val Met
465                 470                 475                 480

His Glu Ala Leu His Asn His Tyr Thr Gln Lys Ser Leu Ser Leu Ser
                485                 490                 495

Pro Gly Lys Lys Asp Pro Lys Phe Trp Val Leu Val Val Val Gly Gly
            500                 505                 510

Val Leu Ala Cys Tyr Ser Leu Leu Val Thr Val Ala Phe Ile Ile Phe
    515                 520                 525

Trp Val Arg Ser Lys Arg Ser Arg Leu Leu His Ser Asp Tyr Met Asn
530                 535                 540

Met Thr Pro Arg Arg Pro Gly Pro Thr Arg Lys His Tyr Gln Ala Tyr
545                 550                 555                 560

Ala Ala Ala Arg Asp Phe Ala Ala Tyr Arg Ser Leu Arg Val Lys Phe
                565                 570                 575

Ser Arg Ser Ala Asp Ala Pro Ala Tyr Gln Gln Gly Gln Asn Gln Leu
            580                 585                 590

Tyr Asn Glu Leu Asn Leu Gly Arg Glu Glu Tyr Asp Val Leu Asp
        595                 600                 605

Lys Arg Arg Gly Arg Asp Pro Glu Met Gly Gly Lys Pro Arg Arg Lys
    610                 615                 620

Asn Pro Gln Glu Gly Leu Tyr Asn Glu Leu Gln Lys Asp Lys Met Ala
625                 630                 635                 640

Glu Ala Tyr Ser Glu Ile Gly Met Lys Gly Glu Arg Arg Arg Gly Lys
                645                 650                 655
```

Gly His Asp Gly Leu Tyr Gln Gly Leu Ser Thr Ala Thr Lys Asp Thr
            660                 665                 670

Tyr Asp Ala Leu His Met Gln Ala Leu Pro Pro Arg
        675                 680

<210> SEQ ID NO 40
<211> LENGTH: 680
<212> TYPE: PRT
<213> ORGANISM: artificial sequence
<220> FEATURE:
<223> OTHER INFORMATION: A5CAR41

<400> SEQUENCE: 40

Met Asp Phe Gln Val Gln Ile Phe Ser Phe Leu Leu Ile Ser Ala Ser
1               5                   10                  15

Val Ile Met Ser Arg Asp Val Lys Leu Val Glu Ser Gly Gly Gly Leu
            20                  25                  30

Val Lys Pro Gly Glu Ser Leu Lys Leu Ser Cys Ile Ala Ser Gly Phe
        35                  40                  45

Thr Phe Ser Asp Tyr Tyr Met Tyr Trp Val Arg Gln Thr Pro Glu Lys
    50                  55                  60

Arg Leu Glu Trp Val Ala Ile Ile Ser Asp Gly Gly Tyr Tyr Thr Tyr
65                  70                  75                  80

Tyr Ser Asp Ile Ile Lys Gly Arg Phe Thr Ile Ser Arg Asp Asn Ala
                85                  90                  95

Lys Asn Asn Leu Tyr Leu Gln Met Ser Ser Leu Lys Ser Glu Asp Thr
            100                 105                 110

Ala Met Tyr Tyr Cys Thr Arg Gly Phe Pro Leu Leu Arg His Gly Ala
        115                 120                 125

Met Asp Tyr Trp Gly Leu Gly Thr Ser Val Thr Val Ser Ser Gly Gly
    130                 135                 140

Gly Gly Ser Gly Gly Gly Gly Ser Gly Gly Gly Gly Ser Asp Ile Gln
145                 150                 155                 160

Met Thr Gln Ser Pro Lys Phe Met Ser Thr Ser Val Gly Asp Arg Val
                165                 170                 175

Ser Val Thr Cys Lys Ala Ser Gln Asn Val Asp Thr Asn Val Ala Trp
            180                 185                 190

Tyr Gln Gln Lys Pro Gly Gln Ser Pro Lys Ala Leu Ile Tyr Ser Ala
        195                 200                 205

Ser Tyr Arg Tyr Ser Asp Val Pro Asp Arg Phe Thr Gly Ser Glu Ser
    210                 215                 220

Gly Thr Asp Phe Thr Leu Thr Ile Ser Asn Val Gln Ser Glu Asp Leu
225                 230                 235                 240

Ala Glu Tyr Phe Cys Gln Gln Tyr Asp Ser Tyr Pro Tyr Thr Phe Gly
                245                 250                 255

Gly Gly Thr Lys Leu Glu Ile Lys Ser Asp Pro Ala Glu Pro Lys Ser
            260                 265                 270

Pro Asp Lys Thr His Thr Cys Pro Pro Cys Pro Ala Pro Pro Val Ala
        275                 280                 285

Gly Pro Ser Val Phe Leu Phe Pro Pro Lys Pro Lys Asp Thr Leu Met
    290                 295                 300

Ile Ala Arg Thr Pro Glu Val Thr Cys Val Val Val Asp Val Ser His
305                 310                 315                 320

Glu Asp Pro Glu Val Lys Phe Asn Trp Tyr Val Asp Gly Val Glu Val
                325                 330                 335

His Asn Ala Lys Thr Lys Pro Arg Glu Gln Tyr Asn Ser Thr Tyr
            340                 345                 350

Arg Val Val Ser Val Leu Thr Val Leu His Gln Asp Trp Leu Asn Gly
        355                 360                 365

Lys Glu Tyr Lys Cys Lys Val Ser Asn Lys Ala Leu Pro Ala Pro Ile
    370                 375                 380

Glu Lys Thr Ile Ser Lys Ala Lys Gly Gln Pro Arg Glu Pro Gln Val
385                 390                 395                 400

Tyr Thr Leu Pro Pro Ser Arg Asp Glu Leu Thr Lys Asn Gln Val Ser
                405                 410                 415

Leu Thr Cys Leu Val Lys Gly Phe Tyr Pro Ser Asp Ile Ala Val Glu
        420                 425                 430

Trp Glu Ser Asn Gly Gln Pro Glu Asn Asn Tyr Lys Thr Thr Pro Pro
    435                 440                 445

Val Leu Asp Ser Asp Gly Ser Phe Phe Leu Tyr Ser Lys Leu Thr Val
        450                 455                 460

Asp Lys Ser Arg Trp Gln Gln Gly Asn Val Phe Ser Cys Ser Val Met
465                 470                 475                 480

His Glu Ala Leu His Asn His Tyr Thr Gln Lys Ser Leu Ser Ser Leu
                485                 490                 495

Ser Pro Gly Lys Lys Ile Tyr Ile Trp Ala Pro Leu Ala Gly Thr Cys
        500                 505                 510

Gly Val Leu Leu Leu Ser Leu Val Ile Thr Leu Tyr Cys Lys Arg Gly
    515                 520                 525

Arg Lys Lys Leu Leu Tyr Ile Phe Lys Gln Pro Phe Met Arg Pro Val
530                 535                 540

Gln Thr Thr Gln Glu Glu Asp Gly Cys Ser Cys Arg Phe Pro Glu Glu
545                 550                 555                 560

Glu Glu Gly Gly Cys Glu Leu Leu Arg Val Lys Phe Ser Arg Ser Ala
                565                 570                 575

Asp Ala Pro Ala Tyr Gln Gln Gly Gln Asn Gln Leu Tyr Asn Glu Leu
        580                 585                 590

Asn Leu Gly Arg Arg Glu Glu Tyr Asp Val Leu Asp Lys Arg Arg Gly
    595                 600                 605

Arg Asp Pro Glu Met Gly Gly Lys Pro Arg Arg Lys Asn Pro Gln Glu
610                 615                 620

Gly Leu Tyr Asn Glu Leu Gln Lys Asp Lys Met Ala Glu Ala Tyr Ser
625                 630                 635                 640

Glu Ile Gly Met Lys Gly Glu Arg Arg Arg Gly Lys Gly His Asp Gly
                645                 650                 655

Leu Tyr Gln Gly Leu Ser Thr Ala Thr Lys Asp Thr Tyr Asp Ala Leu
        660                 665                 670

His Met Gln Ala Leu Pro Pro Arg
    675                 680

<210> SEQ ID NO 41
<211> LENGTH: 729
<212> TYPE: DNA
<213> ORGANISM: artificial sequence
<220> FEATURE:
<223> OTHER INFORMATION: murine sequence scFv A5

<400> SEQUENCE: 41
gacgttaagt tggtggagag tggaggaggt ttggtaaaac caggagaatc ccttaaactc    60
tcttgcattg cctcaggctt tacctttttcc gattattata tgtattgggt ccgacaaaca   120

-continued

```
cccgaaaaac gattggaatg ggttgcaatt atatctgacg gtggctacta cacatattat    180
tctgatatta tcaagggtag atttactatc tccagggata atgccaaaaa taatctctac    240
cttcagatgt cttccctcaa aagtgaagat acggccatgt attattgcac acgcggtttt    300
ccattgctta ggcacggggc aatggattac tggggacttg gtacctccgt cacggtaagt    360
tctggcggtg gcggaagtgg aggcgggggt tctggtggtg gggggtctga catccagatg    420
actcaaagcc ctaaattcat gagcacgtca gttggagatc gagtctccgt tacgtgtaag    480
gcttctcaaa atgtagacac taacgtcgca tggtaccaac agaagccagg ccagtctccg    540
aaagccctga tctacagcgc ttcatacagg tattctgacg tacccgaccg attcactgga    600
tcagagagtg gaactgactt taccettacc atcagcaacg tacaatccga ggatctcgca    660
gaatattttt gccaacagta cgattcctat ccatatactt tcggcggagg cacgaagctt    720
gaaatcaag                                                            729
```

```

<210> SEQ ID NO 42
<211> LENGTH: 243
<212> TYPE: PRT
<213> ORGANISM: Mus musculus
<220> FEATURE:
<223> OTHER INFORMATION: murine scFv A5

<400> SEQUENCE: 42

Asp Val Lys Leu Val Glu Ser Gly Gly Gly Leu Val Lys Pro Gly Glu
1               5                   10                  15

Ser Leu Lys Leu Ser Cys Ile Ala Ser Gly Phe Thr Phe Ser Asp Tyr
            20                  25                  30

Tyr Met Tyr Trp Val Arg Gln Thr Pro Glu Lys Arg Leu Glu Trp Val
        35                  40                  45

Ala Ile Ile Ser Asp Gly Gly Tyr Tyr Thr Tyr Tyr Ser Asp Ile Ile
    50                  55                  60

Lys Gly Arg Phe Thr Ile Ser Arg Asp Asn Ala Lys Asn Asn Leu Tyr
65                  70                  75                  80

Leu Gln Met Ser Ser Leu Lys Ser Glu Asp Thr Ala Met Tyr Tyr Cys
                85                  90                  95

Thr Arg Gly Phe Pro Leu Leu Arg His Gly Ala Met Asp Tyr Trp Gly
            100                 105                 110

Leu Gly Thr Ser Val Thr Val Ser Ser Gly Gly Gly Gly Ser Gly Gly
        115                 120                 125

Gly Gly Ser Gly Gly Gly Gly Ser Asp Ile Gln Met Thr Gln Ser Pro
    130                 135                 140

Lys Phe Met Ser Thr Ser Val Gly Asp Arg Val Ser Val Thr Cys Lys
145                 150                 155                 160

Ala Ser Gln Asn Val Asp Thr Asn Val Ala Trp Tyr Gln Gln Lys Pro
                165                 170                 175

Gly Gln Ser Pro Lys Ala Leu Ile Tyr Ser Ala Ser Tyr Arg Tyr Ser
            180                 185                 190

Asp Val Pro Asp Arg Phe Thr Gly Ser Glu Ser Gly Thr Asp Phe Thr
        195                 200                 205

Leu Thr Ile Ser Asn Val Gln Ser Glu Asp Leu Ala Glu Tyr Phe Cys
    210                 215                 220

Gln Gln Tyr Asp Ser Tyr Pro Tyr Thr Phe Gly Gly Gly Thr Lys Leu
225                 230                 235                 240

Glu Ile Lys
```

<210> SEQ ID NO 43
<211> LENGTH: 2055
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 43

| | | | | | |
|---|---|---|---|---|---|
| ttagcgaggg | ggcagggcct | gcatgtgaag | ggcgtcgtag | gtgtccttgg | tggctgtact | 60 |
| gagaccctgg | taaaggccat | cgtgccccctt | gccctccgg | cgctcgcctt | tcatcccaat | 120 |
| ctcactgtag | gcctccgcca | tcttatcttt | ctgcagttca | ttgtacaggc | cttcctgagg | 180 |
| gttcttcctt | ctcggctttc | cccccatctc | agggtcccgg | ccacgtctct | tgtccaaaac | 240 |
| atcgtactcc | tctcttcgtc | ctagattgag | ctcgttatag | agctggttct | ggccctgctg | 300 |
| gtacgcgggg | gcgtctgcgc | tcctgctgaa | cttcactctc | agggagcgat | aggctgcgaa | 360 |
| gtcgcgtgcg | gcggcatagg | cctggtaatg | cttgcgggtg | ggccccgggc | ggcggggagt | 420 |
| catgttcatg | tagtcactgt | gcaggagcct | gctcctctta | ctcctcaccc | agaaaataat | 480 |
| aaaggccact | gttactagca | agctatagca | agccaggact | ccaccaacca | ccaccagcac | 540 |
| ccaaaatttg | ggatcttttt | tacccggaga | cagggagagg | ctcttctgcg | tgtagtggtt | 600 |
| gtgcagagcc | tcatgcatca | cggagcatga | gaagacgttc | ccctgctgcc | acctgctctt | 660 |
| gtccacggtg | agcttgctgt | agaggaagaa | ggagccgtcg | gagtccagca | cgggaggcgt | 720 |
| ggtcttgtag | ttgttctccg | gctgcccatt | gctctcccac | tccacggcga | tgtcgctggg | 780 |
| atagaagcct | ttgaccaggc | aggtcaggct | gacctggttc | ttggtcagct | catcccggga | 840 |
| tgggggcagg | gtgtacacct | gtggttctcg | gggctgccct | ttggctttgg | agatggtttt | 900 |
| ctcgatgggg | gctgggaggg | ctttgttgga | gaccttgcac | ttgtactcct | tgccattcag | 960 |
| ccagtcctgg | tgcaggacgg | tgaggacgct | gaccacacgg | tacgtgctgt | tgtactgctc | 1020 |
| ctcccgcggc | tttgtcttgg | cattatgcac | ctccacgccg | tccacgtacc | agttgaactt | 1080 |
| gacctcaggg | tcttcgtggc | tcacgtccac | caccacgcat | gtgacctcag | ggtccgggc | 1140 |
| gatcatgagg | gtgtccttgg | gttttggggg | gaagaggaag | actgacggtc | ccgcgactgg | 1200 |
| aggtgctggg | cacggtgggc | atgtgtgagt | tttgtcagga | gatttgggct | cggcgggatc | 1260 |
| cgacttgatt | tcaagcttcg | tgcctccgcc | gaaagtatat | ggataggaat | cgtactgttg | 1320 |
| gcaaaaatat | tctgcgagat | cctcggattg | tacgttgctg | atggtaaggg | taaagtcagt | 1380 |
| tccactctct | gatccagtga | atcggtcggg | tacgtcagaa | tacctgtatg | aagcgctgta | 1440 |
| gatcagggct | ttcggagact | ggcctggctt | ctgttggtac | catgcgacgt | tagtgtctac | 1500 |
| attttgagaa | gccttacacg | taacggagac | tcgatctcca | actgacgtgc | tcatgaattt | 1560 |
| agggctttga | gtcatctgga | tgtcagaccc | ccaccacca | gaaccccgc | ctccacttcc | 1620 |
| gccaccgcca | gaacttaccg | tgacggaggt | accaagtccc | cagtaatcca | ttgccccgtg | 1680 |
| cctaagcaat | ggaaaaccgc | gtgtgcaata | atacatggcc | gtatcttcac | ttttgaggga | 1740 |
| agacatctga | aggtagagat | tattttggc | attatccctg | gagatagtaa | atctaccctt | 1800 |
| gataatatca | gaataatatg | tgtagtagcc | accgtcagat | ataattgcaa | cccattccaa | 1860 |
| tcgttttttcg | ggtgtttgtc | ggacccaata | catataataa | tcggaaaagg | taaagcctga | 1920 |
| ggcaatgcaa | gagagtttaa | gggattctcc | tggttttacc | aaacctcctc | cactctccac | 1980 |
| caacttaacg | tctctagaca | ttatgactga | ggcactgatt | agcaggaagc | tgaaaatctg | 2040 |

```
cacctgaaaa tccat                                                   2055
```

<210> SEQ ID NO 44
<211> LENGTH: 2043
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 44

```
ttagcgaggg ggcagggcct gcatgtgaag ggcgtcgtag gtgtccttgg tggctgtact     60
gagaccctgg taaaggccat cgtgcccctt gcccctccgg cgctcgcctt tcatcccaat    120
ctcactgtag gcctccgcca tcttatcttt ctgcagttca ttgtacaggc cttcctgagg    180
gttcttcctt ctcggctttc ccccatctc agggtcccgg ccacgtctct tgtccaaaac    240
atcgtactcc tctcttcgtc ctagattgag ctcgttatag agctggttct ggccctgctg    300
gtacgcgggg gcgtctgcgc tcctgctgaa cttcactctc agcagttcac atcctccttc    360
ttcttcttct ggaaatcggc agctacagcc atcttcctct tgagtagttt gtactggtct    420
cataaatggt tgtttgaata tatacaggag tttcttcctg ccccgtttgc agtaaagggt    480
gataaccagt gacaggagaa ggaccccaca agtcccggcc aagggcgccc agatgtagat    540 tttttttaccc ggagacaggc tcgagaggct cttctgcgtg tagtggttgt gcagagcctc    600
atgcatcacg gagcatgaga agacgttccc ctgctgccac ctgctcttgt ccacggtgag    660
cttgctgtag aggaagaagg agccgtcgga gtccagcacg ggaggcgtgg tcttgtagtt    720
gttctccggc tgcccattgc tctcccactc cacggcgatg tcgctgggat agaagccttt    780
gaccaggcag gtcaggctga cctggttctt ggtcagctca tcccgggatg ggggcagggt    840
gtacacctgt ggttctcggg gctgcccttt ggctttggag atggttttct cgatggggggc    900 tgggagggct tgttggaga ccttgcactt gtactccttg ccattcagcc agtcctggtg    960
caggacggtg aggacgctga ccacacggta cgtgctgttg tactgctcct cccgcggctt   1020
tgtcttggca ttatgcacct ccacgccgtc cacgtaccag ttgaacttga cctcagggtc   1080
ttcgtggctc acgtccacca ccacgcatgt gacctcaggg gtccgggcga tcatgagggt   1140
gtccttgggt tttgggggga agaggaagac tgacggtccc gcgactggag gtgctgggca   1200
cggtgggcat gtgtgagttt tgtcaggaga tttgggctcg gcgggatccg acttgatttc   1260
aagcttcgtg cctccgccga aagtatatgg ataggaatcg tactgttggc aaaaatattc   1320
tgcgagatcc tcggattgta cgttgctgat ggtaagggta aagtcagttc cactctctga   1380
tccagtgaat cggtcgggta cgtcagaata cctgtatgaa gcgctgtaga tcagggcttt   1440
cggagactgg cctggcttct gttggtacca tgcgacgtta gtgtctacat tttgagaagc   1500
cttacacgta acggagactc gatctccaac tgacgtgctc atgaatttag ggctttgagt   1560
catctggatg tcagaccccc caccaccaga accccgcct ccacttccgc caccgccaga   1620
acttaccgtg acggaggtac caagtcccca gtaatccatt gccccgtgcc taagcaatgg   1680
aaaaccgcgt gtgcaataat acatggccgt atcttcactt ttgagggaag acatctgaag   1740
gtagagatta ttttttggcat tatccctgga gatagtaaat ctacccttga taatatcaga   1800
ataatatgtg tagtagccac cgtcagatat aattgcaacc cattccaatc gttttttcggg   1860 tgtttgtcgg acccaataca tataataatc ggaaaaggta aagcctgagg caatgcaaga   1920
gagtttaagg gattctcctg gttttaccaa acctcctcca ctctccacca acttaacgtc   1980
```

-continued

```
tctagacatt atgactgagg cactgattag caggaagctg aaaatctgca cctgaaaatc    2040
cat                                                                  2043

<210> SEQ ID NO 45
<211> LENGTH: 729
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 45
cttgatttca agcttcgtgc ctccgccgaa agtatatgga taggaatcgt actgttggca      60
aaaatattct gcgagatcct cggattgtac gttgctgatg gtaagggtaa agtcagttcc     120
actctctgat ccagtgaatc ggtcgggtac gtcagaatac ctgtatgaag cgctgtagat     180
cagggctttc ggagactggc ctggcttctg ttggtaccat gcgacgttag tgtctacatt     240
ttgagaagcc ttacacgtaa cggagactcg atctccaact gacgtgctca tgaatttagg     300
gctttgagtc atctggatgt cagacccccc accaccagaa ccccgcctc cacttccgcc      360 accgccagaa cttaccgtga cggaggtacc aagtccccag taatccattg ccccgtgcct     420
aagcaatgga aaaccgcgtg tgcaataata catggccgta tcttcacttt tgagggaaga     480
catctgaagg tagagattat ttttggcatt atccctggag atagtaaatc tacccttgat     540
aatatcagaa taatatgtgt agtagccacc gtcagatata attgcaaccc attccaatcg     600
tttttcgggt gtttgtcgga cccaatacat ataataatcg gaaaaggtaa agcctgaggc     660
aatgcaagag agtttaaggg attctcctgg ttttaccaaa cctcctccac tctccaccaa     720
cttaacgtc                                                            729
```

CHIMERIC ANTIGEN RECEPTORS THAT BIND TO PROSTATE SPECIFIC MEMBRANE ANTIGEN

PRIORITY

This application corresponds to the U.S. National phase of International Application No. PCT/EP2020/086003, filed Dec. 14, 2020, which, in turn, claims priority to European Patent Application No. 19219238.3 filed Dec. 23, 2019, the contents of which are incorporated by reference herein in their entirety.

SEQUENCE LISTING

The instant application contains a Sequence Listing that has been submitted in ASCII format via EFS-Web and is hereby incorporated by reference in its entirety. Said ASCII copy, created on May 15, 2023, is named LNK240US_SL.txt and is 50, 602 bytes in size.

BACKGROUND OF THE INVENTION

The present invention relates to chimeric antigen receptors that bind to tumor antigens whereby the antigen is the prostate specific membrane antigen (PSMA). The chimeric antigen receptors (in the following CAR) are brought into immune cells, in particular T cells, NK cells, iNKT cells and CIK cells, which then specifically react with tumor cells expressing PSMA which leads to the elimination of the tumor cells. The constructs of the present invention contain two major parts. On the one hand the antigen-binding region which specifically binds to the prostate specific membrane antigen (PSMA) and on the other hand co-stimulatory and activating domains derived from a receptor of an immune cell responsible for signal transduction and activation of the immune cell.

Prostate cancer remains the second-most frequently diagnosed cancer among men worldwide with estimated 1.1 million new cases per year. Moreover, with expected 307, 000 deaths, it represents the fifth leading cause of cancer deaths. Whereas primary tumors can successfully be treated, there is no curative treatment for advanced stages. Therefore, new therapeutic options are urgently needed.

The prostate specific membrane antigen (PSMA) is the best characterized antigen in prostate cancer for antibody-based diagnostic and therapeutic intervention. This protein is also known as glutamate carboxypeptidase II (EC 3.4.17.21), N-acetyl-linked acidic dipeptidase I (NAALA-Dase), or folate hydrolase. PSMA is a type II membrane glycoprotein consisting of 750 amino acids (aa) with a small intracellular domain of 19 aa, a transmembrane domain of 24 aa, and a large extracellular domain of 707 aa. The extracellular domain folds into three distinct domains: the protease domain (aa 57-116 and 352-590), the apical domain (aa 117-351), and the C-terminal domain (aa 591-750). It shows a high structural similarity and identity to the human transferrin receptor 1. PSMA is highly restricted to the surface of prostate cancer cells, is present on cancer cells during all tumor stages, and shows an enhanced expression in androgen-independent and metastatic disease. PSMA is not secreted into the extracellular space and undergoes constitutive internalization, which is enhanced by binding of PSMA-specific antibodies. These characteristics make it an ideal candidate for the targeted treatment of local and advanced prostate cancer. Moreover, PSMA was also found to be expressed in the neovascular endothelium of virtually all solid tumor types without expression in normal vascular endothelium. It is therefore considered to be a unique antiangiogenic target.

Monoclonal antibodies (mAbs) are highly specific and versatile tools for cell targeting. In the last decades, they have attracted high interest in medical research and have become the most rapidly expanding class of pharmaceuticals for treating a variety of human diseases including cancer. Antibody 7E11 was the first published PSMA-specific mAb and was found to bind to the N-terminus of the intracellular domain of PSMA. The In-labeled form of 7E11 (ProstaScint, Cytogen, Philadelphia, PA) has received approval from the U.S. Food and Drug Administration (FDA) for the detection and imaging of metastatic prostate cancer in soft tissues. However, because the antibody binds an intracellular epitope, 7E11 is not capable to bind to viable cells. Positive signals in the in vivo imaging with ProstaScint had to be traced back to the detection of dead or dying cells within the tumor masses. Therefore, a new class of anti-PSMA mAbs was generated, which specifically bind to extracellular epitopes of PSMA expressed by living cells.

EP 1 883 698 discloses three different mAbs, 3/A12, 3/E7, 3/F11, which show a strong and specific binding to the extracellular moiety of PSMA on the surface of prostate cancer cells and prostate tissue specimens. In direct comparison with mAb J591, a clinically validated antibody for radioimmunotherapy (PMID:18552139; PMID:24135437; PMID:25771365; PMID: 26175541), the mAb 3/A12 showed higher binding to PSMA expressing C4-2 prostate cancer target cells ($K_d$ [defined as mean half-maximal saturation concentration] of 3/A12=14 nM; $K_d$ of J591=16 nM). Moreover, competitive binding studies demonstrated that mAb 3/A12 binds to a different extracellular PSMA epitope than J591 (PMID:19938014). In an immunohistological study on a panel of human normal tissues, no binding of the 3/A12 mAb to PSMA-negative tissues (adrenal, bone marrow, cerebellum, cerebrum, pituitary, colon, esophagus, heart, kidney, liver, lung, mesothelial cells of the pericardium, nerve, ovary, pancreas, skeletal muscle, skin, spleen, stomach, testis, thymus, thyroid, tonsil, and uterus) was detected. Only binding to secretory cells of the salivary glands and to duodenal brush border cells was observed, which are known to express PSMA (PMID:19938014). The mAb 3/A12 showed a moderate immunoreactivity on acinar secretory epithelial cells of all tested normal prostate tissues. A more intense and extensive staining was noticed in nearly all epithelial cells of adenocarcinomas as well as in lymph node metastases. No immunohistological staining on frozen sections of breast specimen was detected. In contrast and in accordance with other published data, staining of the mammary ductal epithelium was detected with mAb J591. Since PSMA expression in the breast tissue was neither detected by PCR nor by Western blotting, it is likely that mAb J591 cross-reacts with another antigen.

Alzubi et al. gave an oral presentation in October 2018 in Lausanne, Switzerland (Conference on changing the face of modern medicine—Stem cell and gene therapy, Lausanne, Switzerland, Oct. 16-19, 2018). The oral presentation gave only an overview without substantive disclosure. The used antigen binding fragments in the CARs were derived from the monoclonal antibody 3/F11. This monoclonal antibody is different from the monoclonal antibody 3/A12, from which the antigen binding fragments used in the present invention were developed.

The single-chain variable fragment (scFv) A5 (as disclosed in WO 2006/125481) was generated by phage display technique from the mAb 3/A12. The most important fragments for the specificity of the anti-PSMA scFv are the $V_L$ and the $V_H$ parts, which are preferably linked with a polyglycin linker. A5 bound to PSMA-expressing cells with a $K_d$ of about 33 nM.

SUMMARY OF THE INVENTION

According to the present invention the A5 scFv was used for the construction of chimeric antigen receptors (CAR's) to provide constructs for use in immune cells for targeting cancer cells expressing PSMA.

Ma et al. [The Prostate (2014) 74, pp 286-296] disclose a second generation CAR against PSMA comprising a CD28 costimulatory domain and CD3ζ signaling domains and an antigen binding part from a mouse anti-human PSMA monoclonal antibody 3D8 which is commercially available from Northwest Biopharmaceutics, Inc.

Santoro et al. [Cancer Immunol. Res. (2015), pp 68-84] describe T-cells bearing a chimeric antigen receptor against prostate-specific membrane antigen, whereby the PSMA binding portion is derived from the antibody J591.

Zhong et al. [Molecular Therapy (2010), pp. 413-420] disclose also chimeric antigen receptors whereby the PSMA binding fragment is also derived from the antibody J591. The sequence of J591 is well-known in the art. WO 2009/017823 discloses the VH and VL domains thereof.

Hassani et al. (J. Cell Biochem. (2019) 120:10787-10795) discloses the construction of a chimeric antigen receptor bearing a nanobody against PSMA. Nanobodies were used in this publication due to their great homology to human VH family, which should reduce the risk of immunogenic responses of a human antimouse antibody response.

WO 2018/111340 discloses methods for determining potency and proliferative function of chimeric antigen receptor (CAR)-T cells.

Cartellieri et al. (Blood (2015) 126 (23): 5549) describes a chimeric antigen receptor platform, which should overcome the limitations of conventional CAR T cells.

WO 2010/037836 discloses cross-species-specific PSMA×CD3 bispecific single chain antibodies capable of binding to an epitope of human and non-chimpanzee primate CD3YJ.

The antigen-binding fragments are derived from the murine sequences. The murine sequence of the variable domain of the heavy chain (VH) of A5 is shown as SEQ ID NO:1 and the murine sequence of the variable domain of the light chain (VL) of A5 is shown as SEQ ID NO:5. As highly relevant fragments thereof the CDR regions were identified as follows: CDR-H1 as SEQ ID NO:2 having the amino acid sequence of GFTFSDYYM; as CD-H2 (SEQ ID NO:3) IISDGGY and as CDR-H3 (SEQ ID NO:4) GFPLLRHGAMDY. In the light chain the CDRs CDR-L1 (SEQ ID NO:6) has the amino acid sequence KASQNVDTNVA, CDR-L2 (SEQ ID NO:7) has the amino acid sequence SASYRYS and CDR-L3 (SEQ ID NO:8) has the amino acid sequence QQYDSYPYT.

While in the above paragraph the CDRs according to the Kabat numbering system are provided, the CDRs can alternatively also be determined according to the IMGT numbering. The following sequences of the CDRs according to IMGT have been determined: CDR-H1 has been determined as SEQ ID NO:9: GFTFSDYY; SEQ ID NO:10: ISDGGYYT as CDR-H2 and as SEQ ID NO:11 corresponding to CDR-H3: TRGFPLLRHGAMDYWG.

For the light chain the IMGT numbering has been determined for CDR-L1: SEQ ID NO:12: QNVDTN, SEQ ID NO:13 showing CDR-L2: SAS and as SEQ ID NO:14 showing CDR-L3: QQYDSYPYT.

BRIEF DESCRIPTION OF THE FIGURES

FIG. 1 depicts the nucleotide (nt) and amino acid (aa) sequences of a first and second humanized variant of the variable domain of the heavy chain (VH) of A5, namely human A5-VH1 and human A5-VH2, whereby the locations of CDR-H1, CDR-H2 and CDR-H3 are shown according to the determination of IMGT as grey boxes.

FIG. 2 depicts the nucleotide (nt) and amino acid (aa) sequences of a third and fourth humanized variant of the variable domain of the heavy chain (VH) of A5, namely human A5-VH3 and human A5-VH4, whereby the locations of CDR-H1, CDR-H2 and CDR-H3 are shown according to the determination of IMGT as grey boxes.

FIG. 3 depicts the nucleotide (nt) and amino acid (aa) sequences of a fifth humanized variant of the variable domain of the heavy chain (VH) of A5, namely human A5-VH5, whereby the locations of CDR-H1, CDR-H2 and CDR-H3 are shown according to the determination of IMGT as grey boxes.

FIG. 4 depicts the nucleotide (nt) and amino acid (aa) sequences of a first and second humanized variant of the variable domain of the light chain (VL) of A5, namely human A5-VL1 and human A5-VL2, whereby the locations of CDR-L1, CDR-L2, and CDR-L3 are marked with grey boxes.

FIG. 5 depicts the nucleotide (nt) and amino acid (aa) sequences of a third and fourth humanized variant of the variable domain of the light chain (VL) of A5, namely human A5-VL3 and human A5-VL4, whereby the locations of CDR-L1, CDR-L2, and CDR-L3 are marked with grey boxes.

FIG. 6 depicts the nucleotide (nt) and amino acid (aa) sequences of a fifth and sixth humanized variant of the variable domain of the light chain (VL) of A5, namely human A5-VL5 and human A5-VL6, whereby the locations of CDR-L1, CDR-L2, and CDR-L3 are marked with grey boxes.

Figure 7A:
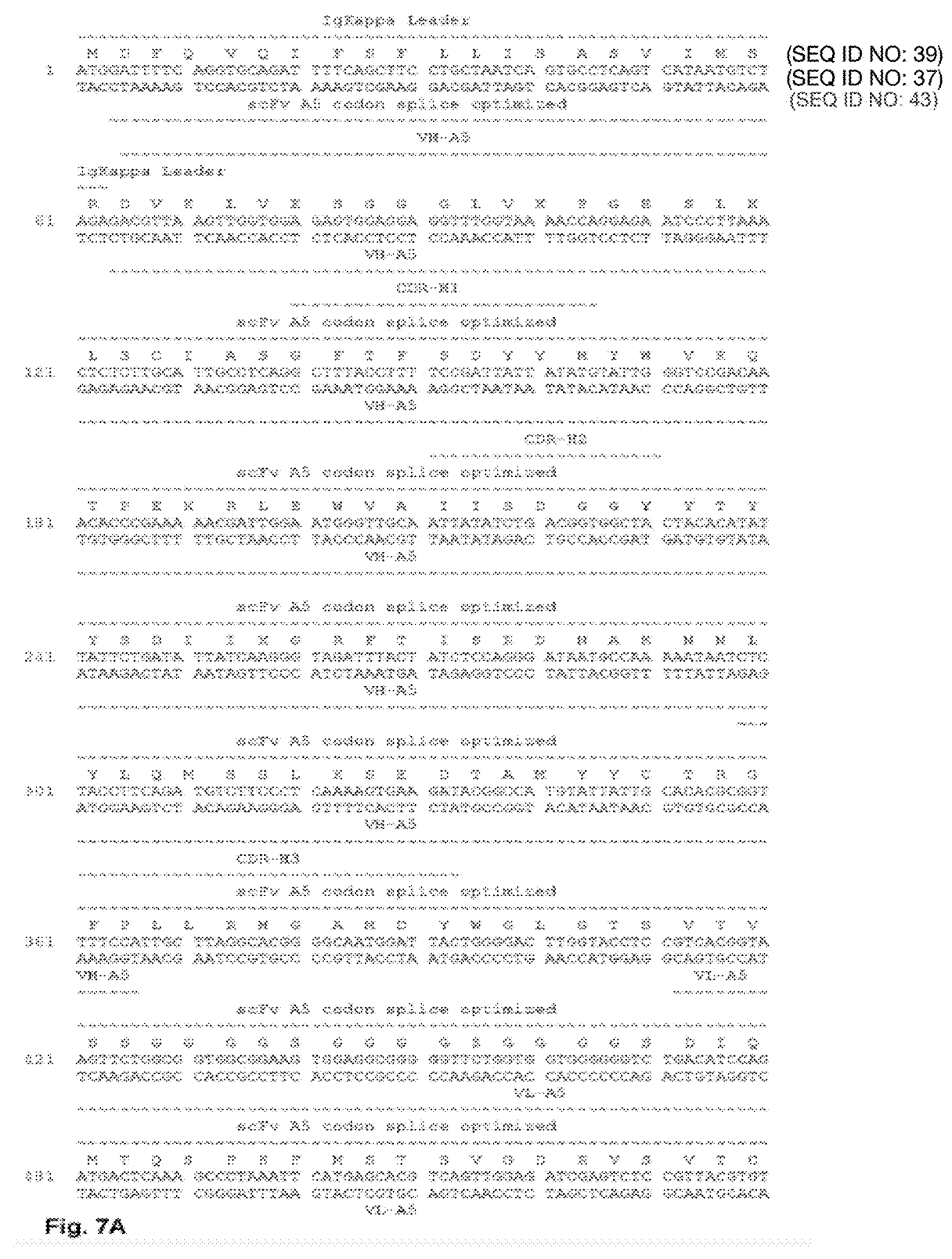
Figure 7B:
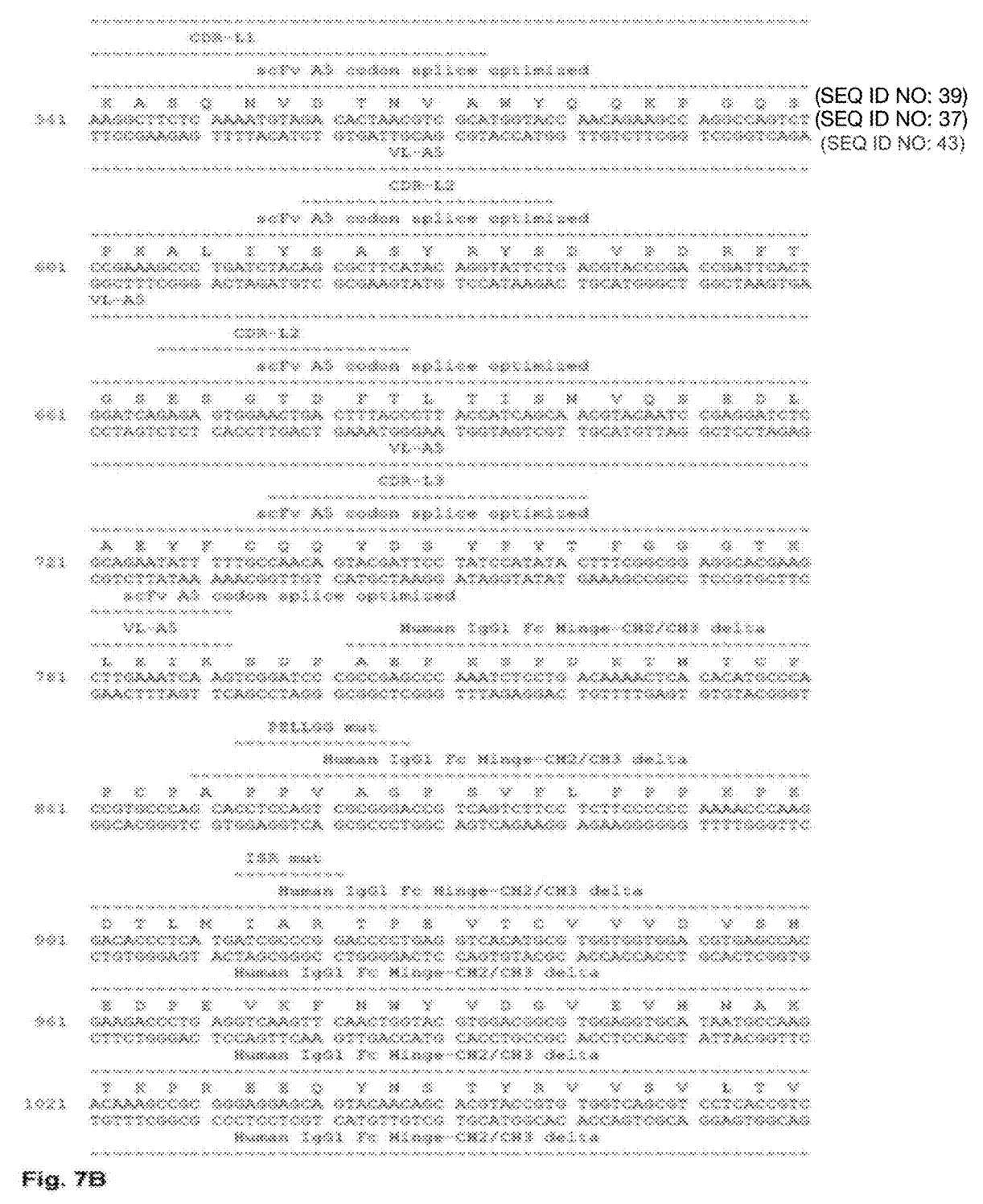
Figure 7C:
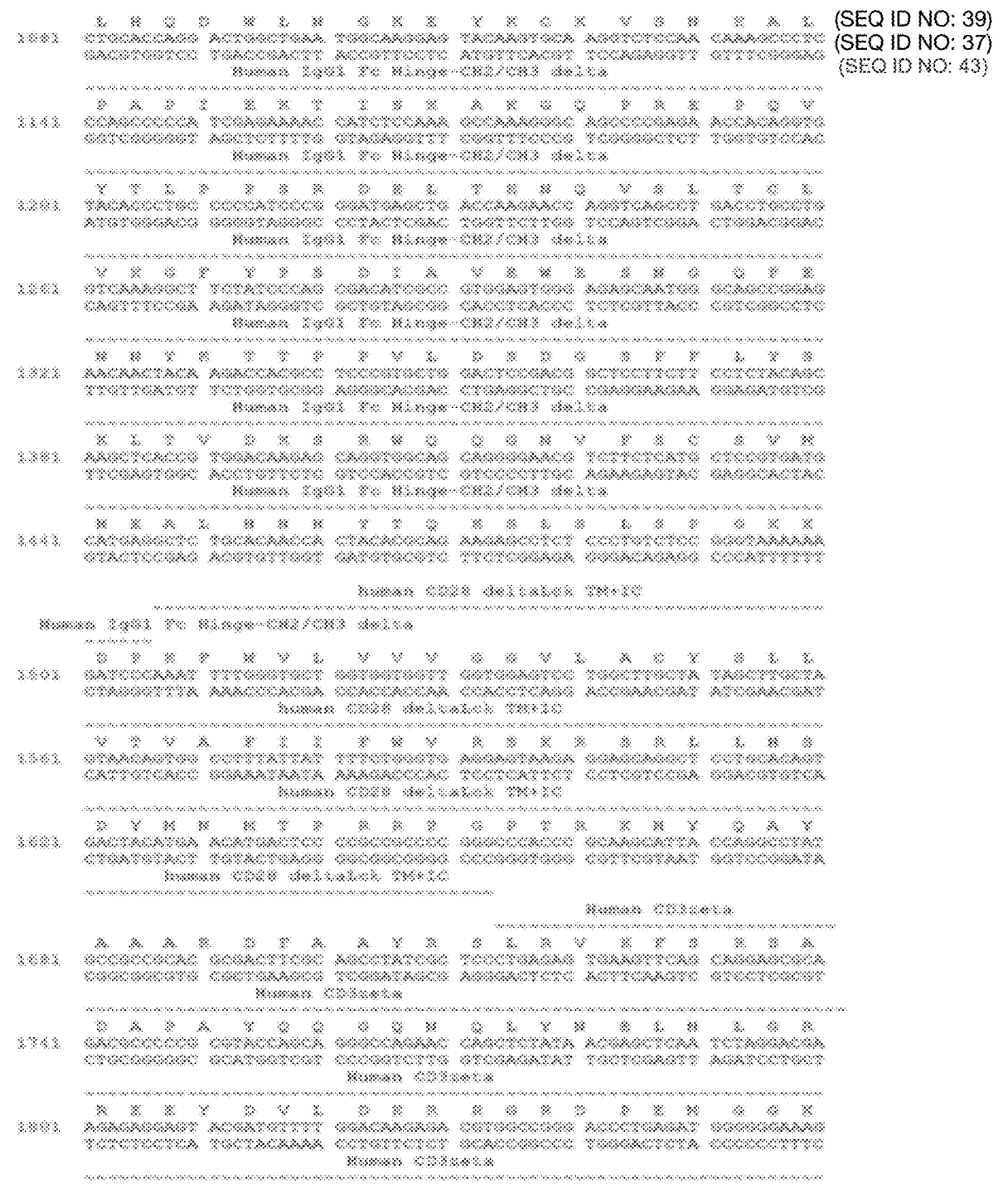
Figure 7D:
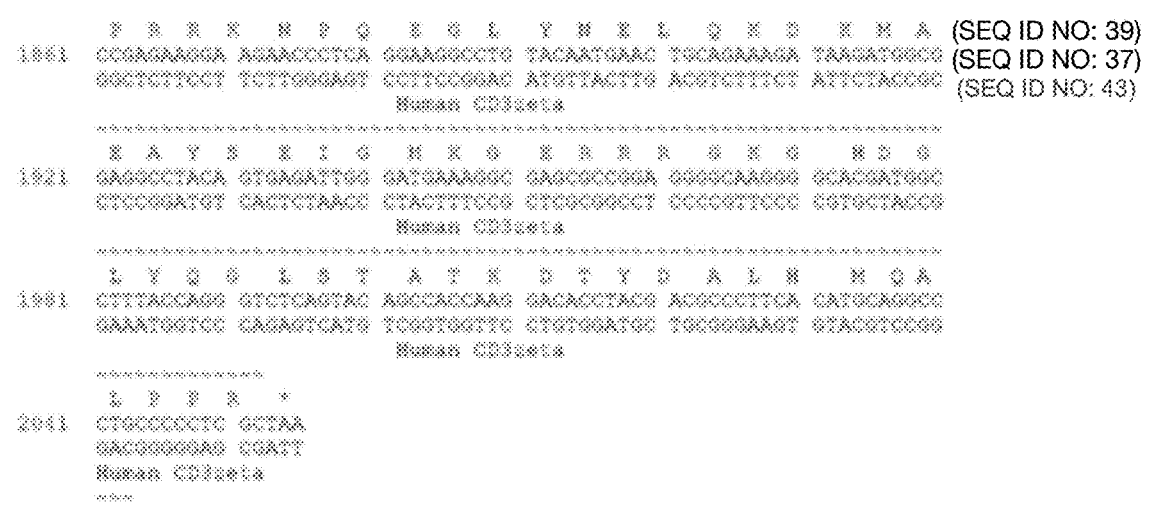

FIGS. 7A-7D present the complete sequence of a preferred embodiment of a construct comprising the scFv A5 antigen binding region. This antigen binding region is linked to the relevant parts of CD28 and CD3ζ. The construct depicted in FIGS. 7A-7D is alternately referred to herein as the "CAR28 construct", "CAR28", and "A5CAR28", the coding sequence for which is set forth in SEQ ID NO: 37. In preferred embodiments of the present invention, the construct sequence is at least 95% identical to the entirety of SEQ ID NO: 37.

FIGS. 8A-8D present the whole construct of the antigen binding fragment scFv A5 which is coupled to the relevant parts of human 4-1BB and CD3ζ. The construct depicted in FIGS. 8A-8D is alternately referred to herein as the "CAR41 construct", "CAR41", and "A5CAR41", the coding sequence for which is set forth in SEQ ID NO: 38. In preferred embodiments of the present invention, the construct sequence is at least 95% identical to the entirety of SEQ ID NO: 38.

FIG. 9 presents a comparison of CAR construct according to the invention with constructs wherein the PSMA antigen binding fragments were already described in the prior art:

Figure 10:
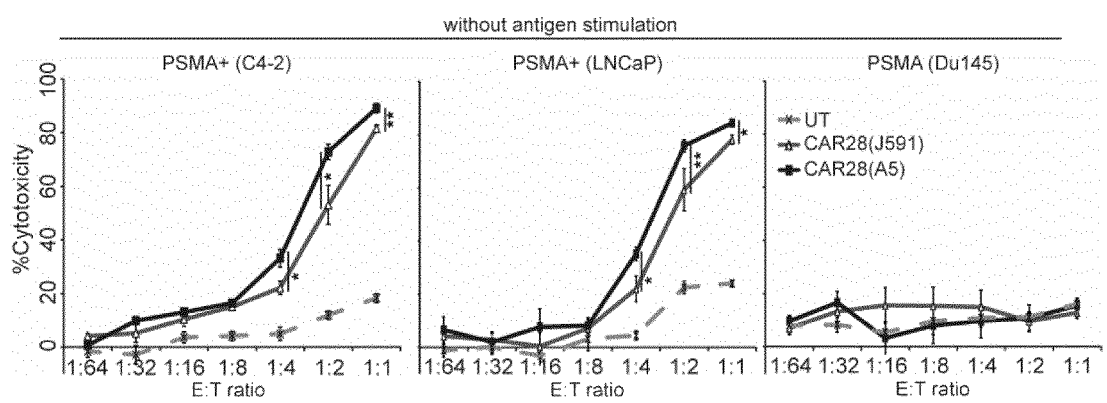

Panel (A) presents a schematic of self-inactivating gamma-retroviral vectors to express $2^{nd}$ generation anti-PSMA CARs. CAR expression is driven by an EFS promoter. The anti-PSMA CARs contain either the single chain variable fragment (scFv) 3D8 or J591 (both described in the prior art), or A5 (derived from murine monoclonal antibody 3/A12 against PSMA), which is fused to an Fc IgG1 derived hinge region, a transmembrane (tm) domain, a CD28 derived costimulatory domain, and an intracellular signaling domain derived from CD3ζ chain. The hinge region provides a physical spacer between the scFv and the tm domains for optimal target recognition. The CD28 costimulatory domain contains amino acid exchanges that prevent LCK binding and enhance anti-tumor activity in the presence of inhibitory regulatory T cells (Tregs). All generated retroviral constructs have the same scaffold but differ only in the scFv fragments allowing for a side-by-side comparison of the CAR constructs with respect to activity and cytotoxicity.

Panel (B) depicts the CAR expression in Jurkat cells were transduced with retroviral particles coding for the three different PSMA-CARs. Following viral transduction, Jurkat cells were expanded for 16-21 days before cells were harvested and stained with anti-human IgG antibody (CAR) to evaluate the transduction efficiencies and the CAR expression levels.

Panel (C) presents the antigen-specific-activation profile, CAR expressing Jurkat cells were stimulated for 24 h at an 1:1 effector-to-target ratio with either PSMA positive, PD-L1 negative C4-2 tumor cells (PSMA+/PDL1−), or PSMA positive, PD-L1 positive LNCaP tumor cells (PSMA+/PDL1+). As a negative control, CAR cells were co-cultured with PSMA negative DU145 tumor cells (PSMA−). Following 24 h stimulation, cells were harvested and activation profile was assessed by evaluating the percentage of cells that are positive for the activation marker CD69. Statistically significant differences are indicated by ****($P<0.001$).

Panel (D) depicts the characterization of employed prostate cancer cell lines. The extent of PSMA target antigen expression (left) and PD-L1 (CD274) expression (right) was assessed on C4-2, LNCaP and DU145 prostate cell lines. For flow cytometric analysis, cells were either stained with 3/F11 1 antibody (anti-PSMA) or an anti-CD274 antibody. UT, untransduced T cells; PD-L1, Programmed cell death ligand 1; PSMA; prostate specific membrane antigen. As shown in panel D (left), both C4-2 and LNCaP tumor cells express the PSMA antigen while the DU145 is negative for the PSMA antigen. Panel D (right) shows that a large fraction of LNCaP and DU145 cells express PD-L1 while C4-2 cells were negative for PD-L1. The antigen-specific activation profiles were compared in A5-based CAR T Jurkat cells side-by-side with J591 and 3D8-based CAR T Jurkat cells. As indicated in Panel C, the A5-based CAR and the J591-based CAR were able to mediate massive activation of the Jurkat cells upon antigen-specific sensitization, as measured by upregulation of the activation marker CD69 in about 70% of cells. Activation was not affected by the presence of the inhibitory ligand PD-L1. On the other hand, the 3D8-based CAR T cells were only weakly activated (up to 20% of CD69-positive cells).

FIG. 10 depicts the functional assessment of PSMA-CAR T cells. Panel (A) presents the cytotoxicity profile of CAR T cells on PSMA positive C4-2 tumor cells. T cells were activated for 2-3 days with anti-CD2/3/28 antibodies prior to retrovirus transduction. CAR T cells were generated by transducing activated T cells with the self-inactivating retroviral vector constructs to express $2^{nd}$ generation anti-PSMA CARs (see FIG. 9, Panel A). Following expansion for 6-9 days without antigen stimulation, CAR T cells were co-cultured for 48 hours at indicated effector to target (E:T) ratios, with either antigen positive C4-2 (PSMA+/PDL1+) or LNCaP (PSMA+/PDL1−) tumor cells or PSMA negative cells (DU145). Cytotoxicity was measured by an XTT ELISA based colorimetric assay (% cytotoxicity=100%-% viability). Statistically significant differences are indicated by *($P<0.05$) or **($P<0.01$). UT, untransduced cells; PSMA, prostate specific membrane antigen. The cytotoxicity profile of the A5-based CAR T cells was compared side-by-side with that of J591-based CAR T cells. A5-based CAR T cells were significantly more cytotoxic as compared to J591-based CAR T cells against both tumor cell targets. This is evidenced by the fact that both tumor cell lines could be eliminated with lower effector-to-target ratios. In conclusion, the A5-based CAR T cells outperformed CAR T cells based on prior art CARs in terms of activation and cytotoxicity.

FIG. 11 depicts the expansion and exhaustion of PSMA targeting CAR T cells:

Panel (A) depicts CAR expression. Following transduction of activated T cells with self-inactivating retroviral vector constructs to express $2^{nd}$ generation anti-PSMA CARs (see FIGS. 9A, 10A), CAR T cells were expanded for 6 days without antigen stimulation (—Ag). In parallel, CAR T cells were expanded and exposed to irradiated PSMA positive (C4-2) cells (+Ag). Expanded CAR T cells were harvested every 3 days and exposed to fresh irradiated antigen positive cells up to 4 times (4×) at effector-target ratio of 1:1. CAR and CD3 expression at indicated exposure times to irradiated PSMA-positive cells were visualized by flow cytometry after staining of cells with antibodies against human IgG (CAR) and CD3. UT, untransduced cells.

Panels (B), (C), and (D) depict CAR T cell expansion. Every 3 days during CAR T cell expansion, cells were harvested and stained with anti-human IgG antibody (CAR) and CD3 to evaluate fraction of CAR-positive cells (B), total cell number (C) and the number of cell divisions (D). Statistically significant differences are indicated by *($P<0.05$). UT, untransduced cells. As shown, multiple exposure to antigen-expressing cells leads to enrichment of CAR positive T cells in the cell population (>95%) for both A5-based CAR T cells as well as J591-based CAR T cells (FIG. 11A-B). However, A5-based CAR T cells expand significantly better upon multiple antigen-specific stimulation as compared to J591-based CAR T cells. This is evident by a -~160-fold increase in the number of total cells at the end of the expansion period (FIG. 11C) as well as a significant increase in the number of cell divisions (FIG. 11D). This data suggest the A5-based CAR T cells exhaust less than J591-based CAR T cells.

Panel (E) depicts the quantitative assessment of CAR T cell phenotype. CAR T cells were stimulated with PSMA-positive C4-2 tumor cells at a 1:1 effector-to-target (E:T) ratio before T cell phenotype profile was assessed based on the expression of CD62L and CD45RA. Shown are T the average percentages of the different T cell subsets from three experiments. Statistically significant differences are indicated by ***($P<0.001$, $n=3$). Tn/Tscm, T cell naïve or T stem cell memory; Tcm, T cell central memory; Tem, T cell effector memory; Teff, T cell effector; UT, untransduced cells.

Panel (F) depicts the quantitative assessment of CAR T cell exhaustion. CAR T cells were stimulated with PSMA-positive C4-2 tumor cells at a 1:1 effector-to-target (E:T) ratio before T cell exhaustion profile was determined based on LAG-3 and PD-1 expression. Shown are the average percentages of PD-1 and LAG3 double-positive or double-negative cells. Statistically significant differences are indicated by ***($P<0.001$, $n=3$). UT, untransduced cells.

This set of experiments addressed the CAR T cell phenotype as well as the exhaustion profiles of the CAR T cells upon antigen stimulation. As seen in panels 3E and 3F, both A5-based and J591-based CAR T cells, respectively, differentiate towards effector cells and exhaust to some extent after antigen exposure. However, the fraction of naïve and memory-type CAR T cells is significantly higher for A5-CAR T cells as compared to J591-based CAR T cells (FIG. 11E). Also, A5-CAR T cells exhaust less frequently upon antigen exposure than J591-based CAR T cells, as indicated by a significantly higher proportion of PD1-negative/LAG3-negative CAR T cells (FIG. 11F). Overall, the CAR T cell phenotype and the exhaustion profile analysis upon antigen exposure indicates a favorable phenotype for A5-CAR T cells over J591-CAR T cells, which correlated with a better expansion of A5-CAR T cells as compared to J591-CAR T cells.

Figure 12:
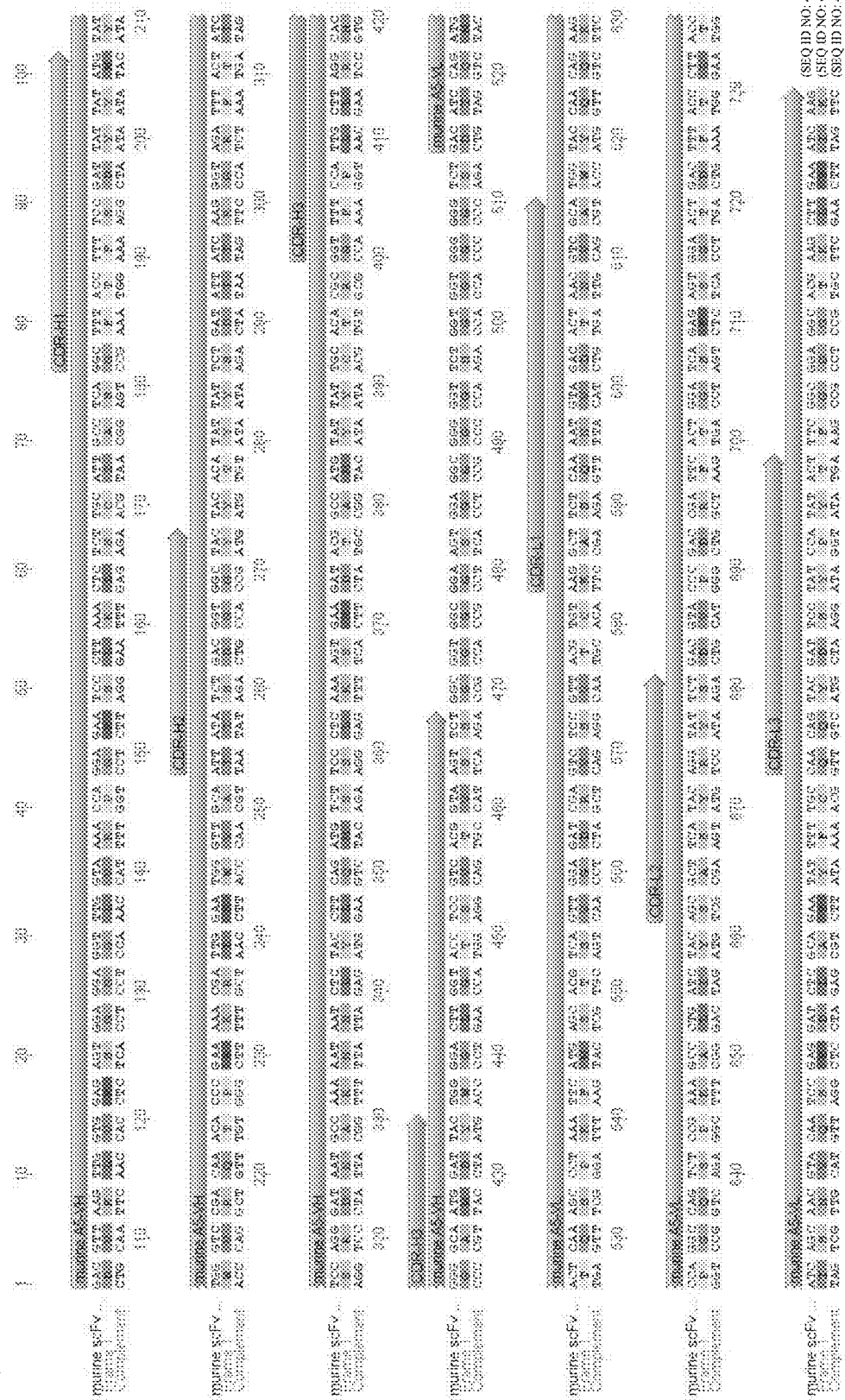

FIG. 12 depicts the sequence (SEQ ID NO:1 and 5) of the murine scFv A5 is provided where by the CDR-H1, CDR-H2, CDR-H3 (SEQ ID NO:2-4), CDR-L1, CDR-L2 and CDR-L3 (SEQ ID NO:6-8) regions according to the Kabat method are shown.

Figure 13A:
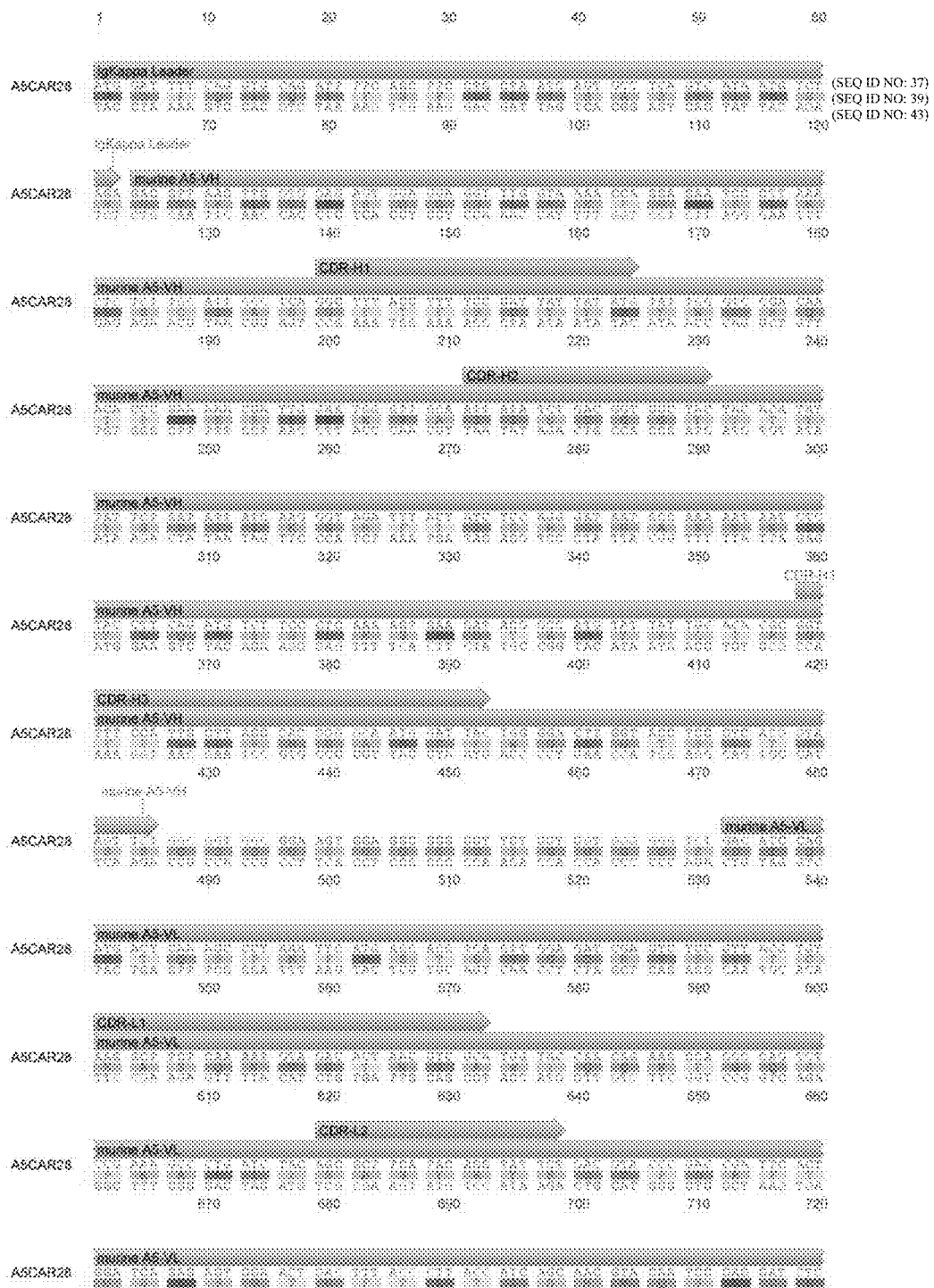
Figure 13B:
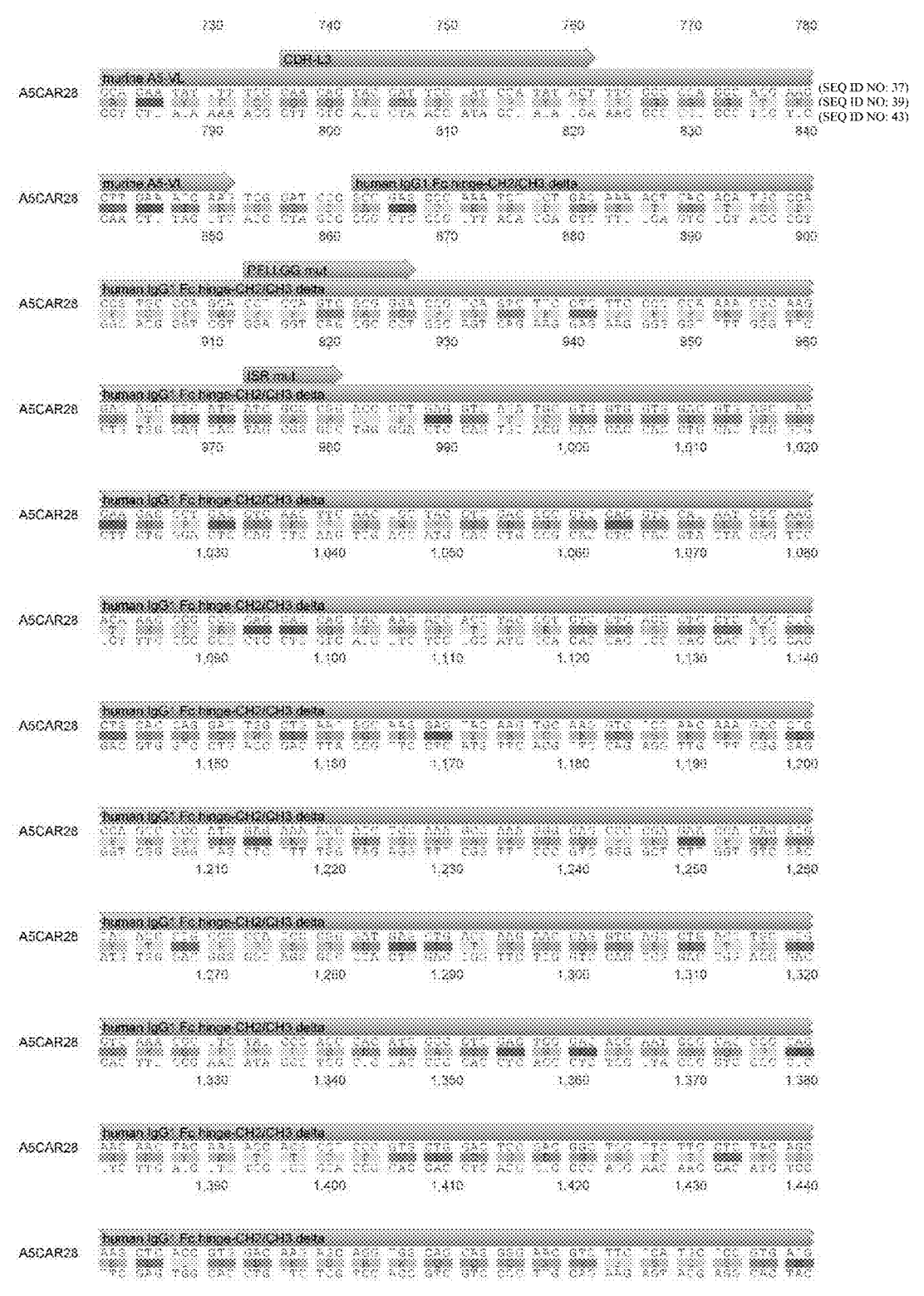
Figure 13C:
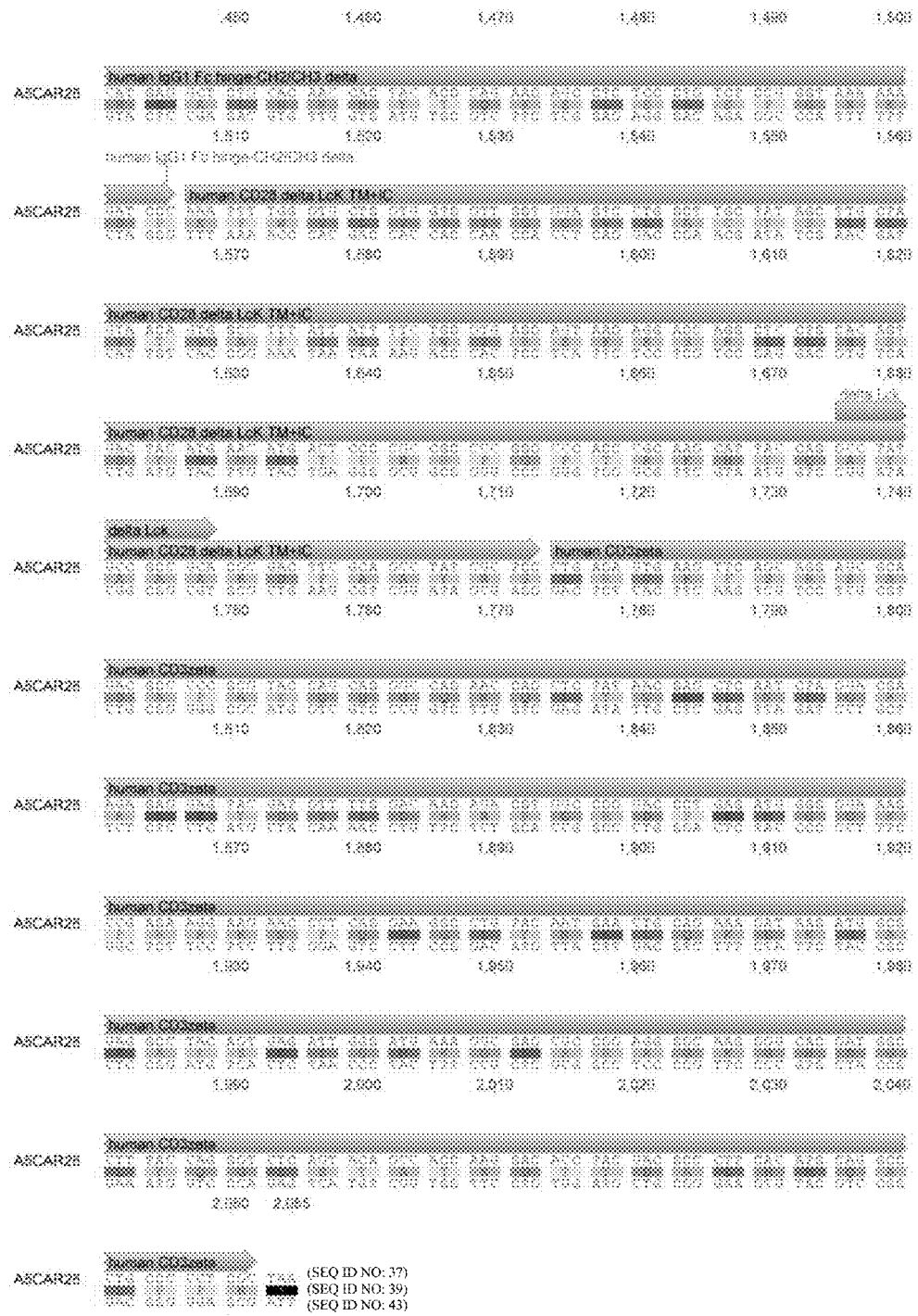

FIGS. 13 A-C show the amino acid sequence ("Frame1") of the CAR construct A5CAR28 including the scFv A5 which is derived from mice. Moreover, the coding nucleic acid sequence and the complementary strand thereof are provided. The CDR H1-H3 and CDR L1-L3 nucleic acid and amino acid sequences are marked with grey arrows.

Figure 14A:
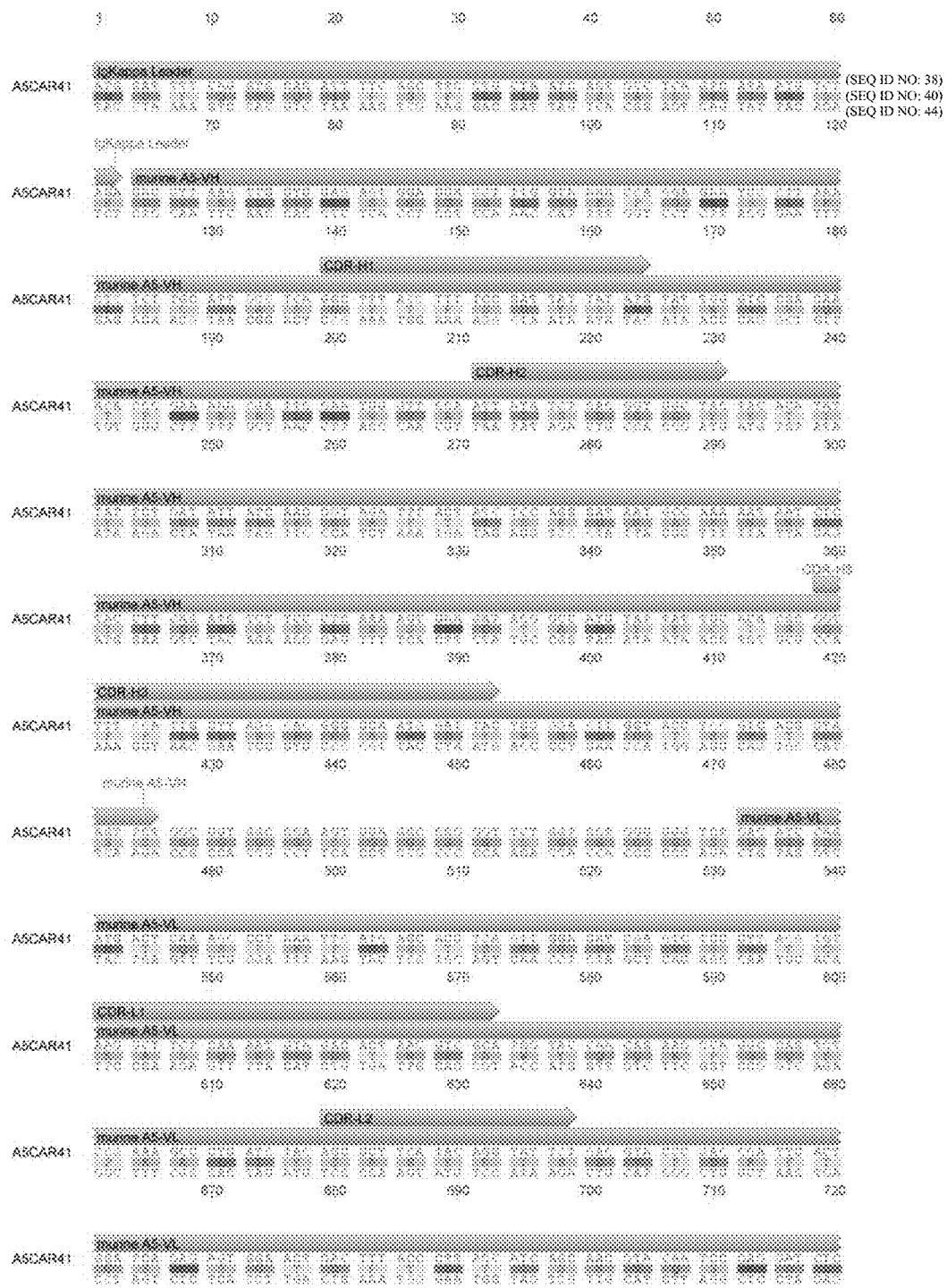
Figure 14B:
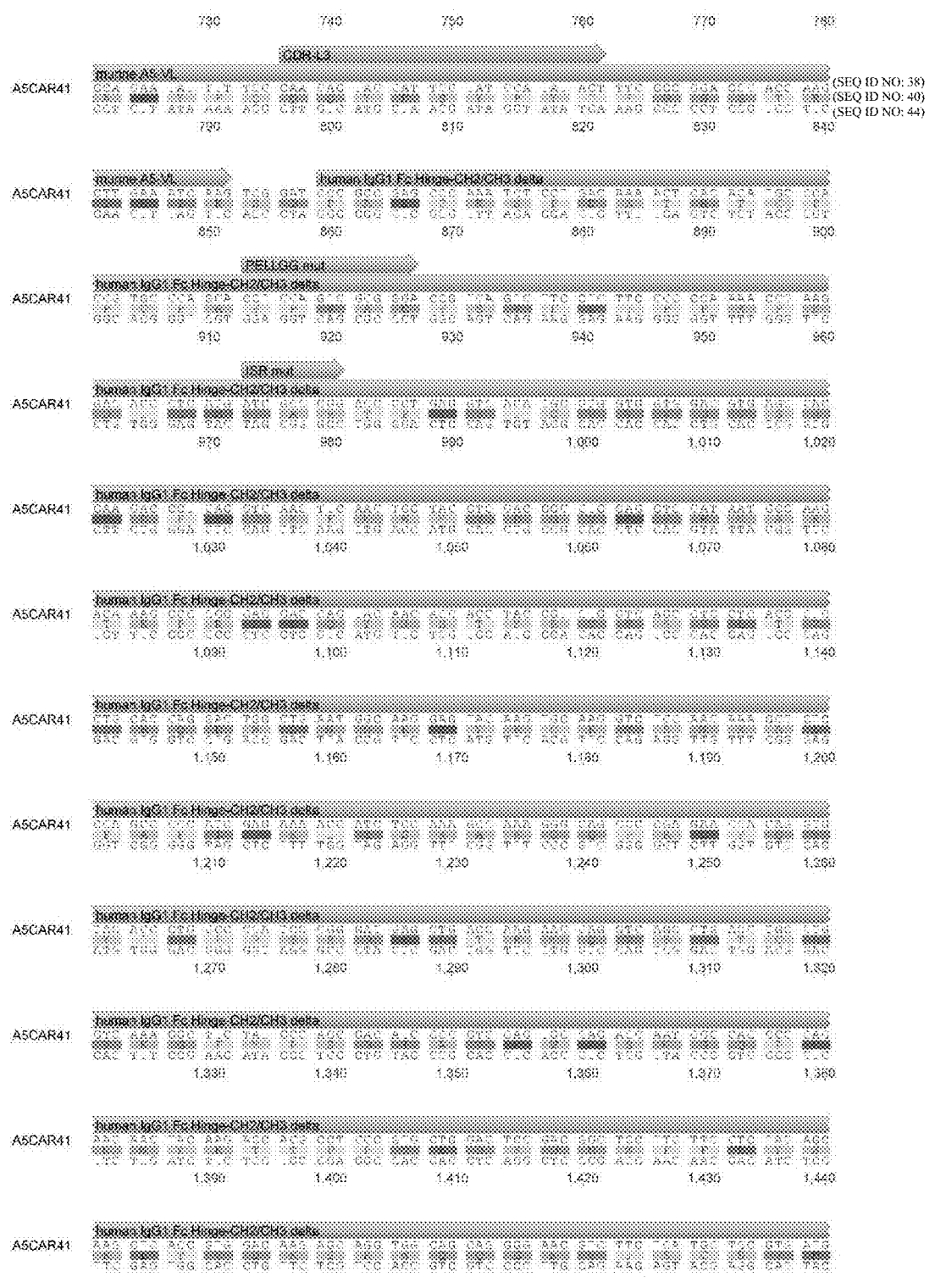
Figure 14C:
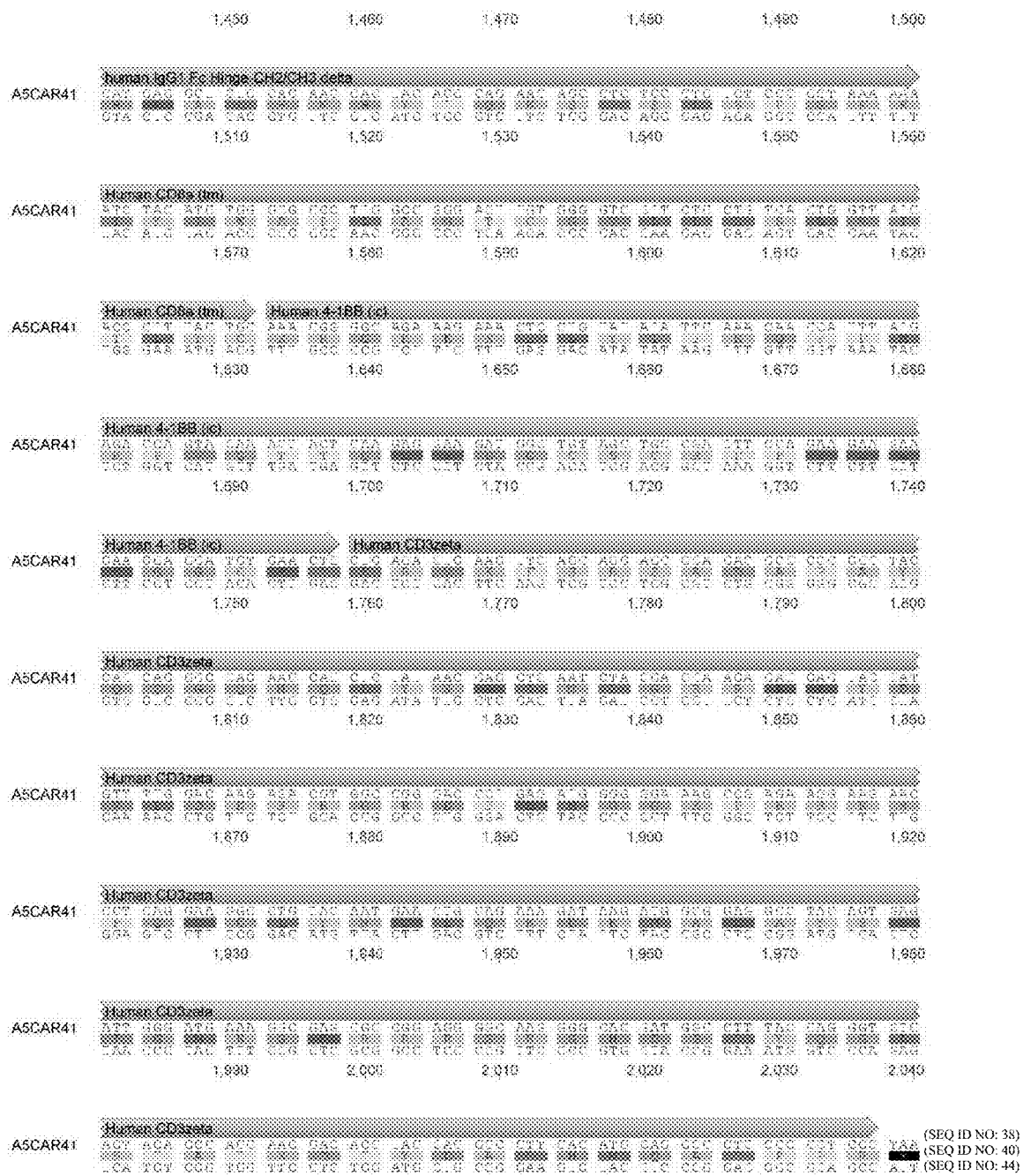

FIGS. 14 A-C show the amino acid sequence ("Frame1") of the CAR construct A5CAR41 including the scFv antigen-binding construct A5 which is derived from mice. Moreover, the coding nucleic acid sequence and the complementary strand thereof are provided. The CDR H1-H3 and CDR L1-L3 nucleic acid and amino acid sequences are marked with grey arrows. The amino acid sequence of the ScFv fragment of A5 is essential for the present invention insofar as it is the starting sequence for the humanization of the antigen binding fragment. The humanized sequences have a homology of at least 80% to SEQ ID NO:1 or/and SEQ ID NO:5, respectively. In a more preferred embodiment the sequences have a homology of at least 90% and more preferred at least 95% to SEQ ID NO:1 and/or SEQ ID NO:5 and even more preferred the homology is at least 98% to SEQ ID NO:1 and/or SEQ ID NO:5. It should be noted that the CDR regions which are shown in FIG. 13 are conserved to a very high level which means that the CDR regions which are determined by the Kabat method have not more than three, preferably not more than one and preferably no amino acid exchange. FIG. 14A shows the sequence of the A5 CAR41 construct and the preferred homology values as lined out above apply also to this construct.

Sequences:

| SEQ ID NO: | nucleic/ amino acid (AA) | description | remarks |
|---|---|---|---|
| 1 | AA | murine VH | |
| 2 | AA | murine CDR-H1 | Kabat |
| 3 | AA | murine CDR-H2 | Kabat |
| 4 | AA | murine CDR-H3 | Kabat |
| 5 | AA | murine VL | |
| 6 | AA | murine CDR-L1 | Kabat |
| 7 | AA | murine CDR-L2 | Kabat |
| 8 | AA | murine CDR-L3 | Kabat |
| 9 | AA | murine CDR-H1 | IMGT |
| 10 | AA | murine CDR-H2 | IMGT |
| 11 | AA | murine CDR-H3 | IMGT |

-continued

| SEQ ID NO: | nucleic/ amino acid (AA) | description | remarks |
|---|---|---|---|
| 12 | AA | murine CDR-L1 | IMGT |
| 13 | AA | murine CDR-L2 | IMGT |
| 14 | AA | murine CDR-L3 | IMGT |
| 15 | nucleic acid | hum A5-VH1 | coding strand |
| 16 | AA | hum A5-VH1 | grey: IMGT-CDR |
| 17 | nucleic acid | hum A5-VH2 | coding strand |
| 18 | AA | hum A5-VH2 | grey: IMGT-CDR |
| 19 | nucleic acid | hum A5-VH3 | coding strand |
| 20 | AA | hum A5-VH3 | grey: IMGT-CDR |
| 21 | nucleic acid | hum A5-VH4 | coding strand |
| 22 | AA | hum A5-VH4 | grey: IMGT-CDR |
| 23 | nucleic acid | hum A5-VH5 | coding strand |
| 24 | AA | hum A5-VH5 | grey: IMGT-CDR |
| 25 | nucleic acid | hum A5-VL1 | coding strand |
| 26 | AA | hum A5-VL1 | grey: IMGT-CDR |
| 27 | nucleic acid | hum A5-VL2 | coding strand |
| 28 | AA | hum A5-VL2 | grey: IMGT-CDR |
| 29 | nucleic acid acid | hum A5-VL3 | coding strand |
| 30 | AA | hum A5-VL3 | grey: IGMT-CDR |
| 31 | nucleic acid | hum A5-VL4 | coding strand |
| 32 | AA | hum A5-VL4 | grey: IGMT-CDR |
| 33 | nucleic acid | hum A5-VL5 | coding strand |
| 34 | AA | hum A5-VL5 | grey: IMGT-CDR |
| 35 | nucleic acid acid | hum A5-VL6 | coding strand |
| 36 | AA | hum A5-VL6 | grey: IGMT-CDR |
| 37 | coding strand | CAR28 construct | FIG. 7 A-D |
| 38 | coding strand | CAR41 construct | FIG. 8 A-D |
| 39 | AA | A5CAR28 | FIG. 7 and 13 |
| 40 | AA | A5CAR41 | FIG. 8 and 14 |
| 41 | nucleic acid | murine scFv A5 | FIG. 12 |
| 42 | AA | murine scFv A5 | FIG. 12 |

DETAILED DESCRIPTION OF THE PREFERRED EMBODIMENTS

Humanization of murine antibodies involves the transfer of beneficial properties (e.g. antigen-specific binding, avoidance of off-target effects by non-crossreactivity with other antigens) from one antibody to another to reduce immunogenicity. Humanization is usually necessary for human use as patients typically respond with an immune reaction against non-human antibodies that can lead to ineffectiveness of treatment and, in the worst-case scenario, to a life-threatening situation. A humanized construct can be derived from the sequence of the antigen-binding fragment shown in SEQ ID NO:1 and 5, respectively. The CDR regions structurally define the paratope, that is, the contact site of the antigen-binding fragment with the antigen. The remainder of the sequence codes for the framework regions, which form the scaffold of the paratope. For the humanization process (e.g. by in silico modeling), the framework sequence is first compared with other antigen-binding sequences derived from humans. Usually a human sequence (acceptor framework) is selected which has the highest similarity with the framework sequence shown of the murine sequence. The CDR regions are grafted into the human acceptor framework to eliminate amino acid sequences which may cause undesired human anti-mouse-antibody (HAMA) immune reactions. Substitutions at potentially critical positions (e.g. amino acids responsible for folding the paratope or the VH-VL interface) are analyzed for prospective back mutations. Even in the CDR sequences exceptional modifications of amino acids may be made to avoid immunogenicity, to ensure the right folding of the paratope, and to maintain the antigen-specific binding.

In the course of the humanization of antibodies preferably a sequence is selected among human immune sequences which have the highest homology with the corresponding murine sequence. Then the location of the CDRs is determined. The determination of the CDRs is well-known in the art and it should be noted that different methods for the determination are known whereby it is possible that the locations of the CDRs differ somewhat. In the course of the present invention the determination of the CDRs according to Kabat was used and also the determination according to the IMGT (International Immunogene Ticks).

In a preferred embodiment of the present invention the humanization was performed according to the so-called "CDR-grafting". The functional CDRs are determined preferably according the IMGT method and those CDRs are transferred in a human framework region which has the highest sequence homology to the starting murine antibody. Then the differences regarding the single amino acids in the framework region of the humanized and murine antibodies were determined with regard to the biochemical properties like size, polarity or charge. In the first step similar amino acids were adapted and successively the different amino acids were changed in order to end up with a complete human framework.

Since the humanized versions disclosed herein have maintained the CDRs either completely or to a very large extent the humanized variants have the same function of the murine antibody whereby, however, the affinity may differ somewhat from each other.

The sequences obtained by the humanization experiments are as SEQ ID NO:15 to 36.

The results of the humanization experiments are shown in FIG. 1 to FIG. 6. It is always the nucleic acid sequence of the coding strand shown. Moreover, the amino acid sequence is provided where by the CDR regions are shown in grey. Those CDR sequences are preferred embodiments of the present invention. It turned out that in most cases for the heavy chains the CDRs were as follows: CDR-H1: GFTFSDYY (SEQ ID NO: 9), CDR-H2: ISDGGYYT (SEQ ID NO: 10) and CDR-H3: TRGFPLLRHGAMDYWG (SEQ ID NO: 11).

For the light chains the following CDRs were preferably used: CDR-L1: QNVDTN (SEQ ID NO: 12), CDR-L2: SAS (SEQ ID NO: 13) and CDR-L3: QQYDSYPYT (SEQ ID NO: 14). The preferred humanized CDRs were deduced from the murine sequences, but adapted to suitable human framework.

In preferred embodiments the humanized antigen binding fragments like preferably scFv fragments or the like have at least three, preferably at least four, more preferably at least five and particularly preferred six CDRs as mentioned above.

For a good maintenance of specific binding to PSMA-positive cells it turned out that in particular the following humanized VH and VL chains should be used: hum A5-VL1, hum A5-VL4, hum A5-VL5 and hum A5-VL6. Those sequences can preferably be combined with any of the humanized sequence hum A5-VH1, hum A5-VH2, hum A5-VH3, hum A5-VH4 and hum A5-VH5; the use of hum A5-VL2 and hum A5-VL3 is less preferred.

In recent years, adoptive immune cell therapy has been introduced as a novel concept to treat different cancers by redirecting the immune system to eliminate the tumor cells. One of the most successful concepts is based on the genetic engineering of T cells to express chimeric antigen receptors (CARs) that bind tumor antigens or tumor-associated antigens in a human leukocyte antigen (HLA)-independent manner. CD19 targeting CAR T cells have been successfully used to treat B cell acute lymphoblastic leukemia (B-ALL), with >90% of patients going into complete remission in several clinical trials. Based on this success, more than 200 clinical trials have been initiated to treat mostly hematological malignancies. For solid tumors, however, the potency of CAR T cell therapy seems rather low to date. The main reason for this failure seems to be the tumor microenvironment (TME), which is the cellular environment in which the tumor exists. It includes various kinds of immune cells, fibroblasts, the extracellular matrix (ECM) as well as the surrounding blood vessels. Many mechanisms that describe restriction of cytotoxic T cell activity in the TME have been described, including the activation of PD-1 based T cell immune checkpoint inhibition. Overcoming these restrictions, combined with T cell checkpoint antagonists, will help to improve anti-tumor activity in the TME.

The tumor eradication, as used in the present invention, requires an adequate survival and intratumoral activation of tumor antigen-specific immune cells, preferably T cells. To meet these requirements T cells must be given appropriate activating signals at the time of antigen-priming and stimulation. The chimeric antigen receptors of the present invention combine therefore an antigen-binding fragment as part of the receptor on T cells. The antigen-binding fragment binds to the specific antigen (here PSMA) to which the T cells should bind. Moreover, the receptors contain sequences from CD28 and 4-1BB, respectively, as co-stimulatory signaling domains. It has been shown that the addition of CD28 sequences, or other co-stimulatory signaling domains, to CD3ζ chain-based receptors increase antigen-induced secretion of interleukin-2 and in vitro T cell expansion. In the present case the signaling domain consists of the CD3ζ domain and either the intracellular CD28 or the 4-1BB domain.

In general, the design of a CAR can vary and meanwhile several generations of CARs are known. The main components of a CAR system are the CD3ζ intracellular domain of the T cell receptor (TCR) complex, the transmembrane domain, the hinge region and the antigen-binding part. In the design of a CAR, the antigen-binding domain is linked to a hinge region, which is also called a spacer region, the transmembrane domain, and a cytoplasmic domain. Those parts are responsible for the position of the antigen-binding part, the attachment in T cell membrane, and intracellular signaling. Besides this structural rule in the CAR design the morphological characteristics of the hinge region, such as their length and sequence, are important for an efficient targeting. The intracellular domain acts as a signal transducer. The cytoplasmic segment of the CD3ζ plays the principal rule due to different functions in activated T cells and the resting ones. However, this cytoplasmic part cannot activate the resting T cells alone. Therefore, there is a need of at least a secondary signal for the full activation of T cells. In the present invention, preferably 4-1BB or CD28 co-stimulatory domains were used. Other co-stimulatory domains, such as co-stimulatory domains derived e.g. from CD27, ICOS and OX40, can be used alternatively.

In preferred embodiments mutations are introduced into the human IgG1 Fc hinge region whereby side effects like preventing LcK activation or an unintended initiation of an innate immune response are avoided. One of those mutations avoids LcK binding and another mutation may inhibit the binding of Treg cells to the construct. Such mutations may improve the biological activity of the construct.

For the treatment of human patients, T cells have to be enriched from the individual patient's peripheral blood (autologous setting) or provided by a donor (allogeneic setting). This can be done for example by leukapheresis. The enriched T cells are then transfected or transduced ex vivo with a suitable vector comprising the genetic information for the CAR.

The genetic information coding for the CAR is inserted into a suitable vector. Such vectors are preferably lentiviral or retroviral vectors. A gold standard for transduction of primary T cells are presently considered lentiviral vectors which seem to be a valid alternative to simpler retroviral vectors. As a further alternative to lentiviral vectors the information can be introduced into the T cells with the help of transposons or plasmids. An alternative to both viral and non-viral delivery are the recently described gene editing tools, designated as CRISPR/Cas or other designer nucleases, such as transcription activator-like effector nucleases (TALENs) or zinc finger nucleases (ZFNs). This technology platforms offer the possibility to target virtually any genomic site in a targeted manner. In the case of CRISPR/Cas, the editing complex comprises a Cas nuclease and a guide RNA, usually composed of a CRISPR RNA (crRNA) and a transacting crRNA. Upon hybridization of the guide RNA to the target sequence, Cas9 (or another Cas nuclease, such as e.g. Cpf1/Cas12a) generates a double-strand break, which can be repaired by non-homologous end joining (NHEJ), an event that can result in a loss of function of the genomic locus. In the presence of a suitable donor DNA, by a mechanism of homology-directed repair (HDR), an exogenous sequence (CAR sequence) can be introduced into the targeted locus. This can be exploited to deliver CAR expression cassette in a desired genomic locus that does not interfere with endogenous gene function and therefore minimizing the genotoxic effects experienced with integrating viral vectors. In a further preferred embodiment, genome editing is used to place the CAR coding sequence under control of an endogenous promoter. The expression from an endogenous promoter, such as the promoter of the TRAC locus, could ensure optimal expression levels of the CAR construct to fulfill its function. The nucleic acid sequence coding for the CARs of the present invention is preferably optimized for the human codon usage. Particularly preferred embodiments are SEQ ID NO:37 coding for the CAR28 construct (FIG. 7 A-D) and SEQ ID NO:38 coding for the CAR41 construct (FIG. 8 A-D).

In another preferred embodiment of the present invention the RNA coding for the CAR construct is introduced into the target cells, such as T-cells. Nucleic acid coding for the CAR construct may be introduced into the target cells by physical procedures, such as electroporation, or by fusion of the cells' membranes with suitable vesicles. In this embodiment, the CAR construct is preferably transiently expressed in the T-cells. The advantage is that there is then a population of transduced T-cells which is present in the treated patient only for a transient time.

In other preferred embodiments the CAR construct is introduced into natural killer cells (NK), invariant natural killer T-cells (iNKT), diverse natural killer cells (dNKT), cytokine-induced killer cells (CIK) or γ-δ T-cells. Furthermore, suitable allogenic cells may be used.

In a further preferred embodiment, in addition to the CAR construct described herein, another transgene that modulates the immune system, such a genes coding for cytokines, chemokine receptors and/or checkpoint inhibitors, may be introduced in the immune cells. In a further preferred embodiment, genome editing is used to disrupt the expression of genes that modulate the immune system, such as genes coding for cytokines, chemokine receptors and/or checkpoint inhibitors.

In another embodiment the constructs according to the present invention and immune cells containing such constructs can be used for local therapy with a targeted tumor injection. In this embodiment, which is performed preferably with automated devices that apply the CAR T-cells to certain places in the body of the patient, where local tumor areas are located. With a biopsy needle a sample is then withdrawn whereby a small cavity is formed. In this cavity the transduced or transfected T-cells are introduced and then the needle is withdrawn. This embodiment is particularly advantageous when there are solid tumors which are extremely difficult to treat with regular methods.

The chimeric antigen receptors disclosed herein can be used for the treatment of diseases which are related to the expression of PSMA. PSMA is expressed in tumor cells derived from prostatic cancer. There are several stages of prostatic cancer known, but it seems that PSMA is one of the markers best suited for the treatment of prostate cancer. The term "prostate cancer" comprises all forms of prostate cancer cells either derived from a primary tumor or from a metastatic tumor or from circulating tumor cells. In a particularly preferred embodiment immune cells engineered with the chimeric antigen receptors of the present invention are used against the neovascularization of solid tumors expressing PSMA.

The chimeric antigen receptor according to the present invention or a nucleic acid coding therefore may be used either as nucleic acid alone or in the format embedded into a vector for the use in the treatment of prostate cancer and prostate derived tumors. The use of a vector, wherein coding nucleic acid is embedded, is a preferred embodiment. The vectors can be used in a manner that they are either introduced into the patient already in a suitable immune cell, preferably a T cell, or they can be applied as nucleic acid, which can enter suitable cells in the patient.

Prostate cancer affects a high percentage of men and causes a very high percentage of cancer deaths. Although the early stages of cancer may be localized to prostate, the disease progresses frequently to metastasis, which affects other organs of the human body, namely bones, liver, limbal system, lung, brain and sometimes also other organs. Metastasis of prostate cancer may be treated by infusing T cells obtained from the patient, which have been transformed with suitable nucleic acids coding for a chimeric antigen receptor according to the present invention. Alternatively, it is also possible to insert such cells specifically to metastatic hotspots in the body of a patient for example by injection. The distribution of the places where the prostate cancer cells are localized can be performed by labelling the areas with suitable detection means, for example antibodies directed against PSMA, which are labeled with a radioactive nuclides sequence scanning of the body of the patient.

In a further embodiment of the present invention immune cells engineered with the chimeric antigen receptors disclosed herein are used in combination with a therapeutic agent, in particular a cytotoxic agent. Cytotoxic agents as used for the treatment of prostate cancer are known. Preferably such substances comprise taxol derivatives, 5-fluorouracil, cyclophosphamide, mitoxantrone, docetaxel, cabazitaxel and etoposide. The following drugs are approved for prostate cancer and preferably used: Abiraterone Acetate, Apalutamide, Bicalutamide, Cabazitaxel, Casodex (Bicalutamide), Degarelix, Docetaxel, Eligard (Leuprolide Acetate), Enzalutamide, Erleada (Apalutamide), Firmagon (Degarelix), Flutamide, Goserelin Acetate, Jevtana (Cabazitaxel), Leuprolide Acetate, Lupron Depot (Leuprolide Acetate), Mitoxantrone Hydrochloride, Nilandron (Nilutamide), Nilutamide, Provenge (Sipuleucel-T), Radium 223 Dichloride, Sipuleucel-T, Taxotere (Docetaxel), Xofigo (Radium 223 Dichloride), Xtandi (Enzalutamide), Zoladex (Gosereliin Acetate), Zytiga (Abiraterone Acetate). It is understood that the chimeric antigen receptors of the present invention can also be used in combination with a medicament used to treat hormone sensitive forms of prostate cancer like for example Leuprolide Acetate.

The preferred embodiments of the present invention are further described and illustrated in the Figures and Examples of the present application. All aspects disclosed in the Figures or the examples, respectively, relate to the present invention unless expressly excluded. The single features of the present invention as disclosed in the experimental part can be combined unless there are technical reasons which speak against such combination. In particular, the Figures show the results of the experiments as follows:

In the Figures and in the experiments the following abbreviations were used:

| Abbreviation | Explanation |
| --- | --- |
| 4-1BB | tumor necrosis factor receptor superfamily member 9 |
| BLI | bioluminescence imaging |
| bw | body weight |
| C4-2 | PSMA positive prostate cancer cell line |
| CAR | Chimeric Antigen Receptor |
| CAR28 | anti-PSMA CAR with CD28 co-stimulatory domain |
| CAR41 | anti-PSMA CAR with 4-1BB co-stimulatory domain |
| CD28 | cluster of differentiation 28 |
| CD3ζ | CD3 zeta region |
| CD45RA | cluster of differentiation 45 isoform RA |
| CD62L | cluster of differentiation 62, L-selectin |
| CR | complete remission |
| DOC, DTX | docetaxel |
| DU145 | PSMA negative prostate cancer cell line |
| EFS | Short version of the elongation factor alpha gene promoter |
| ELISA | enzyme-linked immunosorbent assay |
| i.v. | intravenously |
| i.p. | intraperitoneally |
| S.C. | subcutaneously |
| Gr.A | Granzyme A |
| Gr.B | Granzyme B. |
| IFN-g | Interferon-gamma |
| LcK | lymphocyte-specific protein tyrosine kinase |
| LNCaP | PSMA positive prostate cancer cell line |
| LTR | long terminal repeat of retroviral vector |
| PR | partial remission |
| R | R region of the retroviral long terminal repeat |
| scFv | single chain variable fragment |
| SD | standard deviation |
| Tcm | T cell central memory |
| Teff | T cell effector |
| Tem | T cell effector memory |
| Tn, scm | T cell naïve or T stem cell memory |
| U5 | U5 region of the retroviral long terminal repeat |
| UT | untransduced T cell |
| WPRE | woodchuck hepatitis virus post-transcriptional regulatory element |
| XTT | sodium 3'-[1-(phenylaminocarbonyl)-3,4-tetrazolium]-bis(4-methoxy-6-nitro) benzene sulfonic acid hydrate |
| ΔU3 | deletion in the U3 region in the retroviral long terminal repeat |

It should be mentioned that the sequences disclosed in the specification, the Figures and the sequence protocol and in particular the CDR-Sequences are preferred embodiments of the present invention.

The results of the experiments shown in the Figures can be interpreted as follows:

In general, CARs are composed of an extracellular domain containing the antigen recognizing scFv, a hinge region, a transmembrane region, and one or more intracellular signaling domains that activate the T cell, including the CD3ζ chain. In $2^{nd}$ or $3^{rd}$ generation CARs, co-stimulatory domains, usually derived from CD28, 4-1BB, OX40, CD27 and/or ICOS are included. For the treatment of prostate cancer, many attempts had utilized CARs targeting PSMA epitopes and some of these strategies have already entered clinical trials (e.g. NCT01140373, NCT01929239). However, the potency of these CARs seems to be rather low both in vitro and in vivo. In particular, early studies based on $1^{st}$ generation CARs based on the anti-PSMA scFv 3D8 or J591 (known as Pzl), have shown low potency of the resulting CAR T cells, as indicated by the need of having to employ high effector to target (E:T) ratios up to 100:1 to eliminate the tumor cells in vitro. The in vitro potency improved when $2^{nd}$ or $3^{rd}$ generation CARs based on either D2B or J591 derived scFvs were used. However, the potency of these CAR T cells remained low in xenotransplantion tumor mouse models, as indicated by the fact that the these PSMA targeting CAR T cells were only able to suppress tumor growth but not to eliminate the tumors in vivo, although very high CAR T cell doses, sometimes up to $20 \times 10^6$ CAR T cells, or multiple infusions were applied (PMID 16204083, PMID: 18026115, PMID: 19773745, PMID: 25358763, PMID: 23242161, PMID: 4174378, PMID: 25279468). In view of these mixed results with rather inefficient PSMA-CAR T cells, it was intended to generate and validate novel, more efficient PSMA targeting CARs based on the scFv A5. To this end, a $2^{nd}$ generation PSMA-CAR was designed which harbors a CD28 (CAR28) derived co-stimulatory domain.

A5-based CAR T cells were compared side-by-side with J591 and 3D8-based CAR T cells (FIG. 9). The antigen-specific activation profiles were compared in Jurkat cells transduced with expression vectors coding for A5, J591 and 3D8-based CARs. While the A5-based CAR and the J591-based CAR were able to mediate massive activation of the Jurkat cells upon antigen-specific sensitization (FIG. 9C), 3D8-CAR bearing cells were only weakly activated.

Furthermore, upon transduction of primary T cells, A5-based CAR T cells revealed a superior cytotoxicity profile as compared to J591-based CAR T cells on two PSMA positive tumor cell lines (FIG. 10A), as evidenced by the fact that both tumor cell lines were eliminated with lower effector-to-target ratios. Also, in the presence of antigen bearing tumor cells, the manufactured A5-CAR T cell products expanded better (FIG. 11C), showed less exhaustion (FIG. 11F) and contained a higher percentage of undifferentiated T cells, such as a naïve T cell and T stem cell memory cells (FIG. 11E), as compared to J591-based CAR T cells.

In summary, it has been demonstrated that the A5-based anti-PSMA CAR T cells have unexpected properties that are superior to previously published PSMA-targeting CAR T cells, particularly in view of their superior in vitro cytotoxicity, as well as their T cell phenotype and their expansion and exhaustion profiles upon antigen-specific stimulation. Based on these results, the A5-based CAR T cells are promising tools for the development of novel immunotherapies for the treatment of local and advanced prostate cancer.

The present invention relates therefore to chimeric antigen receptors for T cells which comprise an antigen-binding fragment which binds specifically to the PSMA antigen. The antigen-binding fragment comprises preferably a $V_H$ and a $V_L$ fragment which are connected with a suitable linker. Moreover, the chimeric antigen receptor comprises preferably a spacer element, a transmembrane fragment and a CDR3ζ cytoplasmic domain. Furthermore, the chimeric antigen receptor preferably comprises a fragment from the CD28 and/or a 4-1 BB cytoplasmic domain.

The chimeric antigen receptors of the present invention contain preferably at least three CDRs selected from the group consisting of CDR-H1, CDR-H2, CDR-H3, CDR-L1, CDR-L2 and CDR-L3. The CDRs are shown by grey arrows above the amino acid sequence and the relevant nucleic acid sequence coding. In a preferred embodiment the chimeric antigen receptor comprises at least three (CDR-H1, CDR-H3, CDR-L3), preferably four (CDR-H1, CDR-H3, CDR-L2, CDR-L3), and more preferred at least five (CDR-H1, CDR-H3, CDR-L1, CDR-L2, CDR-L3) of the CDRs.

The chimeric antigen receptors are preferably present in a humanized format. Such a humanized format can be obtained by inserting the at least three, preferably four, more preferred five or six CDRs into a suitable human antigen-binding scaffold having a high homology to the murine scaffold as shown in FIG. 1-6.

Example 1

Preparation of CAR Encoding Retroviral Particles

HEK293T cells were cultured at 37° C. in a humidified incubator with 5% $CO_2$ in DMEM (Gibco, Invitrogen, Karlsruhe, Germany) supplemented with 10% fetal calf serum (Biochrom, Berlin, Germany), penicillin (100 U/ml), streptomycin (100 mg/L) and 10 mM HEPES (Sigma-Aldrich). One day prior to transfection, cells were seeded in 10 cm dishes at cell density of $5\times10^6$ cells/dish. 24 h later, cells were transfected using polyethylenimine (PEI: 0.1 mg PEI/ml, Polyscience Inc., USA). Per 10 cm dish, 3 μg of a plasmid encoding the VSV-G envelope, 6 μg of a gag/pol encoding plasmid, and 10 μg of a vector plasmid coding for the individual CAR constructs (FIG. 9A) were used. 48 h and 72 h post-transfection, supernatants containing viral vectors were collected and concentrated using ultracentrifugation (WX ultra series; Thermo Scientific: 25,000 rpm for 2 hours at 4° C.). Concentrated vectors were suspended in 100 μl of cold PBS and kept at −80° C. until used.

Biological titers of the vector preparations were determined by transducing Jurkat T cells, followed by staining of the transduced cells with anti-human IgG to determine the fraction of CAR positive cells.

Example 2

Generation of PSMA-Targeting CAR T Cells

Peripheral blood mononuclear cells (PBMCs) were isolated using phase separation (Ficoll, Sigma-Aldrich) according to the manufacture's recommendation and then frozen in liquid nitrogen until used. For generation of CAR T cells, PBMCs were thawed and let to recover for 24 h in RPMI complete medium [RPMI 1640 medium (Gibco, Invitrogen, Karlsruhe, Germany) supplemented with 10% fetal calf serum (Biochrom, Berlin, Germany), penicillin (100 U/ml), streptomycin (100 mg/L) and 10 mM HEPES buffer (Sigma-Aldrich)]. Then, PBMCs were activated using anti-CD2/CD3/CD28 antibodies (Immunocult, StemCell Technologies) and cultured in RPMI complete medium supplemented with 100 U/ml of IL-2, 25 U/ml of IL-7 and 50 U/ml of IL-15 (all from Miltenyi Biotech) for 2 to 3 days before transduction with gamma-retroviral constructs encoding either of the PSMA targeting CAR T cells with a dose ranging from 50-300 transducing units per cell. Transduced cells were cultured in wells coated with poly-D-lysin (PDL, Sigma-Aldrich) containing RPMI complete medium supplemented with 5 μg/ml of protamine sulfate (Sigma-Aldrich) and 1000 U/ml of IL-2, 25 U/ml of IL-7 and 50 U/ml of IL-15. After one day, medium was changed and cells were further expanded for 8-9 days in RPMI complete medium supplemented with 100 U/ml of IL-2, 25 U/ml of IL-7 and 50 U/ml of IL-15 before being frozen in liquid nitrogen until further use.

Example 3

Cell Activation Upon Antigen Stimulation

The biological activity of a preferred construct according to the present invention has been compared with a construct wherein the PSMA binding fragment is derived from the antibody J591. Furthermore, it was compared with a similar construct wherein the antigen binding construct was derived from another antibody (3D8).

The constructs were introduced into Jurkat T-cell line and the CAR expression level was determined by flow cytometry after staining of cells with anti-human IgG. As shown in FIG. 9B, all CAR constructs were properly expressed in Jurkat T-cells. UT (untransduced cells) served as a negative control for staining.

The antigen-specific activation of transduced Jurkat T cells was measured by monitoring the expression of the activation marker CD69 upon antigen stimulation FIG. 9C. As opposed to A5 and J591-based CARs, respectively, the 3D8-based CAR mediated only weak activation of the transduced Jurkat cells upon exposure to antigen positive cells. This was independent of the expression of the inhibitory ligand PD-L1. None of the CAR constructs were activated when they were stimulated with antigen negative (DU145) cells.

Example 4

Expansion of PSMA-Targeting CAR T Cells

CAR T cells were generated from PBMCs following retroviral transduction as described in example 2. At day 6 post-transduction, CAR T cells were co-cultured with irradiated PSMA positive (C4-2) tumor positive cells for 12 days at a 1:1 effector-to-target ratio in RPMI complete medium supplemented with 100 U/ml of IL-2, 25 U/ml of IL-7 and 50 U/ml of IL-15 (all from Miltenyi Biotech). Every 3 days, cells were harvested, counted and plated over fresh irradiated antigen positive (C4-2) tumor positive cells. To determine CAR expression levels and the fraction of CAR-positive cells by flow cytometry (FACS Canto II or Accuri, BD Biosciences), cells were stained with anti-human IgG-PE (Southern Biotech).

The number of CAR T cells was counted at different time points using a NucleoCounter (NC-250, ChemoMetec). The number of cell divisions was calculated based on the absolute cell number.

Furthermore, the quality of CAR T cells was determined by flow cytometric analysis to check the CAR T cell phenotype and the CAR T cell exhaustion pattern.

Example 5

Quality Assessment of Expanded CAR T Cells

For quality assessment, CAR T cells were exposed to antigen positive (C4-2) tumor cells before cells were harvested and stained with anti-human CD62L-Bv421 (BD Biosciences), anti-human CD45RA-FITC (Biolegend), anti-human CD3-APC/H7 (BD Biosciences) and anti-human IgG-PE (CAR) (Southern Biotec). The T cell phenotype was determined based on the expression of CD62L and CD45RA. Cells were pre-gated on CD3+/CAR− for untransduced (UT) T cells or on CD3+/CAR+ for both types of CAR T cells (not shown). It was observed that the A5-CAR T cells were less differentiated as compared to J591CAR T cells as indicated by the presence of high proportion of undifferentiated cells naïve T cell (Tn) and T stem cell memory (Tscm) but a low proportion of effector T cells (Teff).

Example 6

CAR T Cell Exhaustion Upon Antigen Stimulation

To monitor CAR T cell exhaustion upon antigen specific stimulation, CAR T cells were exposed to PSMA-positive tumor cells (C4-2) before being harvested and stained with anti-human CD279-FITC (PD-1, BD Biosciences), anti-human CD223-eFluor710 (LAG-3, BD Biosciences), anti-human CD3-APC/H7 (BD Biosciences) and anti-human IgG-PE (Southern Biotec). The exhaustion profile was determined by flow cytometry (FACS Canto II) based on the expression of CD279 (PD-1) and CD223 (LAG-3). Cells were pre-gated either on CD3+/CAR− for UT T cells or CD3+/CAR+ for both types of CARs (not shown). As compared to J591-CAR T cells, A5-CAR T cells maintained a significantly increased number of LAG-3 and PD-1 double negative cells upon antigen encounter, indicating a less exhausted T cell phenotype.

Together, the data of examples 4 and 5 and 6 indicate that antigen exposure was a major determinant of CAR T cell phenotype, CAR T cell expansion and CAR T cell exhaustion. A5-CAR T cells outperformed J591-CAR T cells in all of these assays.

Example 7

In Vitro Cytotoxicity of Manufactured PSMA-CAR T Cells

The cytotoxic potential of PSMA targeting CAR T cells was determined by assessing their ability to kill PSMA positive tumor cells using a cell viability XTT assay. CAR T cells were co-cultured with either PSMA-positive (C4-2) or (LNCaP) tumor cells or antigen-negative tumor control cells (DU145) in 96 well plates for 48 h at different effector-to-target ratios in a final volume of 200 μl/well of RPMI complete medium without any cytokines. To determine cell viability as a function of metabolic activity, 100 μl/well of medium was removed and replaced with 100 μl/well of XTT solution (Sigma-Aldrich), and cells incubated at 37° C. Colorimetric changes were quantified using an ELISA reader (Infinite F50, Tecan) at 450 nm. Cytotoxicity is indicated as the percentage of dead cells, which equals 100% minus the percentage of viable cells. Viability was calculated according to the equation $[OD_{E+T}-OD_{E\ only}]/[OD_{T\ only}-OD_{medium\ only}]$ (E, effector cells=CAR T cells; T, target cells=tumor cells). A5-CAR T cells were able to eliminate the tumor positive cells at a significantly lower effector-to-target ratio as compared to the J591-CAR T cells. The results demonstrate that A5-CAR T cells outperformed J591-CAR T cells in this in vitro cytotoxicity assay.

Usually the genetic information coding for the chimeric antigen receptor is introduced with the help of a suitable vector into the target immune cells (e.g. T cell). Such a vector can preferably be a lentivirus vector or a retroviral vector or a transposon or a plasmid. Alternatively, the genetic information can be introduced into the genome of the T cell in a targeted fashion with the help of designer nuclease technology, such as the CRISPR/Cas technology or the TALEN technology, as described herein.

In a further aspect the present invention relates to an in vitro method of providing T cells comprising a chimeric antigen receptor as described herein. In the first step T cells are isolated from a donor preferably by leukapheresis methods. This results in a substantial enrichment of the T cells. The T cells are then genetically modified by transfection with a suitable vector or by transduction with a viral vector containing the genetic information for the chimeric antigen receptor, respectively. Such genetically modified T cells can then be isolated and amplified whereby those T cells which do not contain the desired genetic information can be separated from the modified T cells or at least reduced. The transfected T cells can then be applied to the patient to be treated.

The invention claimed is:

1. A humanized chimeric antigen receptor (CAR) comprising:
    (a) an antigen-binding fragment which binds specifically to a prostate specific membrane antigen (PSMA), wherein said antigen-binding fragment against said PSMA contains the following 6 QDR sequences: GFTFSDYY (SEQ ID NO: 9) as CDR-H1, ISDGGYYT (SEQ ID NO: 10) as CDR-H2, TRGFPLLRHGAMDYWG (SEQ ID NO: 11) as CDR-H3, QNVDTN (SEQ ID NO: 12) as CDR-L1, SAS (SEQ ID NO: 13) as CDR-L2 and QQYDSYPYT (SEQ ID NO: 14) as CDR-L3,
    (b) a transmembrane domain,
    (c) an intracellular signaling domain comprising a CD3ζ cytoplasmic domain,
    (d) a co-stimulatory domain comprising a CD28 and/or a 4-1BB cytoplasmic domain, and
    (e) an Fc IgG1 derived hinge region disposed between the antigen-binding fragment of part (a) and the transmembrane domain of part (b) so as to provide a physical spacer therebetween for optimal target recognition.

2. The humanized chimeric antigen receptor according to claim 1 characterized in that said chimeric antigen receptor contains at least one humanized light chain selected from the group consisting of SEQ ID NO:26, SEQ ID NO:28, SEQ ID NO:30, SEQ ID NO:32, SEQ ID NO:34, and SEQ ID NO:36 or at least one heavy chain having an amino acid sequence selected from the group consisting of SEQ ID NO:16, SEQ ID NO:18, SEQ ID NO:20, SEQ ID NO:22, and SEQ ID NO:24.

3. A nucleic acid coding for the humanized chimeric antigen receptor according to claim 1.

4. A vector coding for the humanized chimeric antigen receptor according to claim 1, characterized in that said vector contains a nucleic acid coding for said humanized chimeric antigen receptor.

5. A vector coding for a chimeric antigen receptor characterized in that said vector comprises SEQ ID NO:37, SEQ ID NO:38, or a sequence which is at least 95% identical to the entirety of SEQ ID NO: 37 or SEQ ID NO: 38.

6. An in vitro method of providing immune cells that express the humanized chimeric antigen receptor according to claim 1, said method comprising the steps of:
    (i) isolating immune cells from a donor by leukapheresis;
    (ii) transfecting/transducing the immune cells with a vector containing a nucleic acid coding for said humanized chimeric antigen receptor; and
    (iii) isolating and amplifying the transfected/transduced immune cells that express said humanized chimeric antigen receptor.

7. An immune cell containing the genetic information coding for the humanized chimeric antigen receptor according to claim 1.

8. The humanized chimeric antigen receptor according to claim 1 or a nucleic acid coding for said humanized chimeric antigen receptor or a vector containing such a nucleic acid formulated for use in the treatment of prostate cancer and/or prostate-derived tumors.

9. An agent having anti-tumor activity comprising the humanized chimeric antigen receptor according to claim 1, a nucleic acid coding for said humanized chimeric antigen receptor, and/or a vector containing such a nucleic acid formulated for use in the treatment of solid tumor expressing PSMA, wherein said agent is introduced into the solid tumor.

10. A method of treating prostate cancer, a prostate-derived tumor, or a solid tumor expressing PSMA in a subject in need thereof, said method comprising the steps of administering to said subject transfected/transduced immune cells isolated and amplified by the method of claim 6 simultaneously or contemporaneously with the administration of (a) one or more chemotherapeutically active agents selected from the group consisting of taxol derivatives, 5-fluorouracil, cyclophosphamide, mitoxantrone, docetaxel and capacitaxel, and/or (b) one or more biopharmaceutical agents selected from the group consisting of protein kinase inhibitors, enzyme inhibitors, anti-genomic therapeutics, and T cell checkpoint antagonists.

11. The immune cells of claim 7, wherein said immune cells are selected from the group consisting of T-cells, natural killer cells (NK), invariant natural killer T-cells (iNKT), diverse natural killer cells (dNKT), cytokine-induced killer cells (CIK) and γ-δ T-cells.

12. A humanized chimeric antigen receptor (CAR) that consists essentially of:
   a. an antigen-binding fragment that binds specifically to a prostate specific membrane antigen (PSMA), wherein said antigen-binding fragment against said PSMA contains the following 6 DR sequences: GFTFSDYY (SEQ ID NO: 9) as CDR-H1, ISDGGYYT (SEQ ID NO: 10) as CDR-H2, TRGFPLLRHGAMDYWG (SEQ ID NO: 11) as CDR-H3, QNVDTN (SEQ ID NO: 12) as CDR-L1, SAS (SEQ ID NO: 13) as CDR-L2 and QQYDSYPYT (SEQ ID NO: 14) as CDR-L3,
   b. a transmembrane domain,
   c. a CD3ζ cytoplasmic domain acting as an intracellular signaling domain,
   d. at least one co-stimulatory domain selected from the group consisting of a CD28 and 4-1BB cytoplasmic domain, and
   e. an Fc IgG1 derived hinge region disposed between the antigen-binding fragment of part (a) and the transmembrane domain of part (b) so as to provide a physical spacer therebetween for optimal target recognition.

* * * * *